(12) United States Patent
Maurer et al.

(10) Patent No.: US 7,727,232 B1
(45) Date of Patent: Jun. 1, 2010

(54) FLUID-ASSISTED MEDICAL DEVICES AND METHODS

(75) Inventors: Christopher W. Maurer, Wakefield, MA (US); Eric W. Conley, South Berwick, ME (US); Arnold E. Oyola, Northborough, MA (US)

(73) Assignee: Salient Surgical Technologies, Inc., Portsmouth, NH (US)

( * ) Notice: Subject to any disclaimer, the term of this patent is extended or adjusted under 35 U.S.C. 154(b) by 960 days.

(21) Appl. No.: 11/051,090

(22) Filed: Feb. 4, 2005

(51) Int. Cl.
*A61B 18/14* (2006.01)
(52) U.S. Cl. .......................................... 606/48; 606/50
(58) Field of Classification Search ............. 606/48–50, 606/45
See application file for complete search history.

(56) References Cited

U.S. PATENT DOCUMENTS

| | | | |
|---|---|---|---|
| 623,022 A | 4/1899 | Johnson | |
| 1,735,271 A | 11/1929 | Groff | |
| 1,814,791 A | 7/1931 | Ende | |
| 2,002,594 A | 5/1935 | Wappler et al. | |
| 2,031,682 A | 2/1936 | Wappler et al. | |
| 2,102,270 A | 12/1937 | Hyams | |
| 2,275,167 A | 3/1942 | Bierman | |
| 2,888,928 A | 6/1959 | Seiger | |
| 3,163,166 A | 12/1964 | Brant et al. | |
| 3,682,130 A | 8/1972 | Jeffers | |
| 3,750,650 A | 8/1973 | Ruttgers | |
| 3,901,241 A | 8/1975 | Allen, Jr. | |
| 3,987,795 A * | 10/1976 | Morrison | 606/48 |
| 4,037,590 A | 7/1977 | Dohring et al. | |
| 4,060,088 A | 11/1977 | Morrison, Jr. et al. | |
| 4,116,198 A | 9/1978 | Roos | |
| 4,244,371 A | 1/1981 | Farin | |
| 4,276,874 A | 7/1981 | Wolvek et al. | |
| 4,301,802 A | 11/1981 | Poler | |
| 4,307,720 A | 12/1981 | Weber, Jr. | |
| 4,321,931 A | 3/1982 | Hon | |
| 4,326,529 A | 4/1982 | Doss et al. | |
| 4,342,218 A | 8/1982 | Fox | |
| 4,355,642 A | 10/1982 | Alferness | |
| 4,381,007 A | 4/1983 | Doss | |
| 4,532,924 A | 8/1985 | Auth et al. | |
| 4,548,207 A | 10/1985 | Reimels | |
| 4,567,890 A | 2/1986 | Ohta et al. | |
| 4,602,628 A | 7/1986 | Allen, Jr. | |
| 4,671,274 A | 6/1987 | Sorochenko | |
| 4,674,499 A | 6/1987 | Pao | |
| 4,920,982 A | 5/1990 | Goldstein | |

(Continued)

FOREIGN PATENT DOCUMENTS

DE          1 007 960          5/1957

(Continued)

*Primary Examiner*—Roy D Gibson
(74) *Attorney, Agent, or Firm*—Grossman, Tucker, Perreault & Pfleger, PLLC

(57) ABSTRACT

A bipolar electrosurgical scraper device is provided comprising a handle, a blade having a thickness and a beveled distal end with the beveled distal end terminating distally in a scraping edge. The beveled distal end includes a first electrode and a second electrode with the first electrode and the second electrode provided along a width of the blade and spaced apart with respect to the thickness of the blade. The device also comprises a fluid passage at least one fluid outlet in fluid communication with the fluid passage.

20 Claims, 9 Drawing Sheets

U.S. PATENT DOCUMENTS

| | | |
|---|---|---|
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,976,711 A | 12/1990 | Parins et al. |
| 4,985,030 A | 1/1991 | Melzer et al. |
| 4,998,933 A | 3/1991 | Eggers et al. |
| 5,009,656 A | 4/1991 | Reimels |
| 5,013,312 A | 5/1991 | Parins et al. |
| 5,035,696 A | 7/1991 | Rydell |
| 5,071,419 A | 12/1991 | Rydell et al. |
| 5,080,660 A | 1/1992 | Buelna |
| 5,122,138 A | 6/1992 | Manwaring |
| 5,125,928 A | 6/1992 | Parins et al. |
| 5,147,357 A | 9/1992 | Rose et al. |
| 5,151,102 A | 9/1992 | Kamiyama et al. |
| 5,156,613 A | 10/1992 | Sawyer |
| 5,167,659 A | 12/1992 | Ohtomo et al. |
| 5,171,311 A | 12/1992 | Rydell et al. |
| 5,190,541 A | 3/1993 | Abele et al. |
| 5,195,959 A | 3/1993 | Smith |
| 5,197,963 A | 3/1993 | Parins |
| 5,197,964 A | 3/1993 | Parins |
| 5,217,460 A | 6/1993 | Knoepfler |
| 5,234,428 A | 8/1993 | Kaufman |
| 5,242,441 A | 9/1993 | Avitall |
| 5,242,442 A | 9/1993 | Hirschfeld |
| 5,269,780 A | 12/1993 | Roos |
| 5,269,781 A | 12/1993 | Hewell, III |
| 5,277,696 A | 1/1994 | Hagen |
| 5,281,215 A | 1/1994 | Milder |
| 5,281,216 A | 1/1994 | Klicek |
| 5,282,799 A | 2/1994 | Rydell |
| 5,290,286 A | 3/1994 | Parins |
| 5,300,087 A | 4/1994 | Knoepfler |
| 5,313,943 A | 5/1994 | Houser et al. |
| 5,318,589 A | 6/1994 | Lichtman |
| 5,322,503 A | 6/1994 | Desai |
| 5,330,521 A | 7/1994 | Cohen |
| 5,334,193 A | 8/1994 | Nardella |
| 5,342,357 A | 8/1994 | Nardella |
| 5,342,359 A | 8/1994 | Rydell |
| 5,348,554 A | 9/1994 | Imran et al. |
| 5,364,394 A | 11/1994 | Mehl |
| 5,383,874 A | 1/1995 | Jackson et al. |
| 5,383,876 A | 1/1995 | Nardella |
| 5,395,312 A | 3/1995 | Desai |
| 5,395,363 A | 3/1995 | Billings et al. |
| 5,401,272 A | 3/1995 | Perkins |
| 5,403,311 A | 4/1995 | Abele et al. |
| 5,403,312 A | 4/1995 | Yates et al. |
| 5,405,344 A | 4/1995 | Williamson et al. |
| 5,405,376 A | 4/1995 | Mulier et al. |
| 5,417,672 A | 5/1995 | Nita et al. |
| 5,417,709 A | 5/1995 | Slater |
| 5,431,168 A | 7/1995 | Webster, Jr. |
| 5,431,649 A | 7/1995 | Mulier et al. |
| 5,433,708 A | 7/1995 | Nichols et al. |
| 5,437,662 A | 8/1995 | Nardella |
| 5,437,664 A | 8/1995 | Cohen et al. |
| 5,441,498 A | 8/1995 | Perkins |
| 5,441,503 A | 8/1995 | Considine et al. |
| 5,445,638 A | 8/1995 | Rydell et al. |
| 5,456,682 A | 10/1995 | Edwards et al. |
| 5,456,684 A | 10/1995 | Schmidt et al. |
| 5,458,596 A | 10/1995 | Lax et al. |
| 5,458,597 A | 10/1995 | Edwards et al. |
| 5,458,598 A | 10/1995 | Feinberg et al. |
| 5,460,629 A | 10/1995 | Shlain et al. |
| 5,462,521 A | 10/1995 | Brucker et al. |
| 5,472,441 A | 12/1995 | Edwards et al. |
| 5,472,443 A | 12/1995 | Cordis et al. |
| 5,487,385 A | 1/1996 | Avitall |
| 5,490,819 A | 2/1996 | Nicholas et al. |
| 5,500,012 A | 3/1996 | Brucker et al. |
| 5,514,130 A | 5/1996 | Baker |
| 5,522,815 A | 6/1996 | Durgin, Jr. et al. |
| 5,536,267 A | 7/1996 | Edwards et al. |
| 5,540,562 A | 7/1996 | Giter |
| 5,542,928 A | 8/1996 | Evans et al. |
| 5,542,945 A | 8/1996 | Fritzsch |
| 5,558,671 A | 9/1996 | Yates |
| 5,562,503 A | 10/1996 | Ellman et al. |
| 5,562,703 A | 10/1996 | Desai |
| 5,564,440 A | 10/1996 | Swartz et al. |
| 5,569,242 A | 10/1996 | Lax et al. |
| 5,569,243 A | 10/1996 | Kortenbach et al. |
| 5,573,424 A | 11/1996 | Poppe |
| 5,573,533 A | 11/1996 | Strul |
| 5,575,810 A | 11/1996 | Swanson et al. |
| 5,584,872 A | 12/1996 | LaFontaine et al. |
| 5,599,346 A | 2/1997 | Edwards et al. |
| 5,599,350 A | 2/1997 | Schulze et al. |
| 5,605,539 A | 2/1997 | Buelna et al. |
| 5,609,151 A | 3/1997 | Mulier et al. |
| 5,633,578 A | 5/1997 | Eggers et al. |
| 5,637,110 A | 6/1997 | Pennybacker et al. |
| 5,640,955 A | 6/1997 | Ockuly et al. |
| 5,643,197 A | 7/1997 | Brucker et al. |
| 5,647,869 A | 7/1997 | Goble et al. |
| 5,647,871 A | 7/1997 | Levine et al. |
| 5,653,692 A | 8/1997 | Masterson et al. |
| 5,660,836 A | 8/1997 | Knowlton |
| 5,676,662 A | 10/1997 | Fleischhacker et al. |
| 5,676,693 A | 10/1997 | LaFontaine |
| 5,681,282 A | 10/1997 | Eggers et al. |
| 5,683,366 A | 11/1997 | Eggers et al. |
| 5,683,384 A | 11/1997 | Gough et al. |
| 5,687,723 A | 11/1997 | Avitall |
| 5,688,270 A | 11/1997 | Yates et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,702,386 A | 12/1997 | Stern et al. |
| 5,709,680 A | 1/1998 | Yates et al. |
| 5,713,896 A | 2/1998 | Nardella |
| 5,718,241 A | 2/1998 | Ben-Haim et al. |
| 5,718,701 A | 2/1998 | Shai et al. |
| 5,718,703 A | 2/1998 | Chin |
| 5,722,400 A | 3/1998 | Ockuly et al. |
| 5,725,524 A | 3/1998 | Mulier et al. |
| 5,730,127 A | 3/1998 | Avitall |
| 5,735,846 A | 4/1998 | Panescu et al. |
| 5,743,903 A | 4/1998 | Stern et al. |
| 5,746,739 A | 5/1998 | Sutter |
| 5,749,869 A | 5/1998 | Lindenmeier et al. |
| 5,755,717 A | 5/1998 | Yates et al. |
| 5,755,753 A | 5/1998 | Knowlton |
| 5,766,153 A | 6/1998 | Eggers et al. |
| 5,766,167 A | 6/1998 | Eggers et al. |
| 5,785,705 A | 7/1998 | Baker |
| 5,785,706 A | 7/1998 | Bednarek |
| 5,792,140 A | 8/1998 | Tu et al. |
| 5,797,905 A | 8/1998 | Fleischman et al. |
| 5,797,960 A | 8/1998 | Stevens et al. |
| 5,800,413 A | 9/1998 | Swartz et al. |
| 5,800,482 A | 9/1998 | Pomeranz et al. |
| 5,807,393 A | 9/1998 | Williamson et al. |
| 5,807,395 A | 9/1998 | Mulier et al. |
| 5,810,764 A | 9/1998 | Eggers et al. |
| 5,810,805 A | 9/1998 | Sutcu et al. |

| | | | | | | |
|---|---|---|---|---|---|---|
| 5,810,811 A | 9/1998 | Yates et al. | | 6,048,333 A | 4/2000 | Lennox et al. |
| 5,817,093 A | 10/1998 | Williamson et al. | | 6,053,172 A | 4/2000 | Hovda et al. |
| 5,823,956 A | 10/1998 | Roth et al. | | 6,053,912 A | 4/2000 | Panescu et al. |
| 5,827,271 A | 10/1998 | Buysse et al. | | 6,056,744 A | 5/2000 | Edwards |
| 5,827,281 A | 10/1998 | Levin | | 6,056,745 A | 5/2000 | Panescu et al. |
| 5,833,703 A | 11/1998 | Manushakian | | 6,056,747 A | 5/2000 | Saadat et al. |
| 5,843,019 A | 12/1998 | Eggers et al. | | 6,059,781 A | 5/2000 | Yamanashi et al. |
| 5,843,021 A | 12/1998 | Edwards et al. | | 6,063,079 A | 5/2000 | Hovda et al. |
| 5,843,078 A | 12/1998 | Sharkey | | 6,063,081 A | 5/2000 | Mulier et al. |
| 5,843,152 A | 12/1998 | Tu et al. | | 6,066,134 A | 5/2000 | Eggers et al. |
| 5,855,614 A | 1/1999 | Stevens et al. | | 6,066,139 A | 5/2000 | Ryan et al. |
| 5,860,951 A | 1/1999 | Eggers et al. | | 6,068,627 A | 5/2000 | Orszulak et al. |
| 5,860,974 A | 1/1999 | Abele | | 6,068,653 A | 5/2000 | LaFontaine |
| 5,861,002 A | 1/1999 | Desai | | 6,071,280 A | 6/2000 | Edwards et al. |
| 5,861,021 A | 1/1999 | Thome et al. | | 6,073,051 A | 6/2000 | Sharkey et al. |
| 5,868,739 A | 2/1999 | Lindenmeier et al. | | 6,074,389 A | 6/2000 | Levine et al. |
| 5,871,469 A | 2/1999 | Eggers et al. | | 6,080,151 A | 6/2000 | Swartz et al. |
| 5,871,524 A | 2/1999 | Knowlton | | 6,081,749 A | 6/2000 | Ingle et al. |
| 5,873,855 A | 2/1999 | Eggers et al. | | 6,083,237 A | 7/2000 | Huitema et al. |
| 5,876,398 A | 3/1999 | Mulier et al. | | 6,086,585 A | 7/2000 | Hovda et al. |
| 5,888,198 A | 3/1999 | Eggers et al. | | 6,086,586 A | 7/2000 | Hooven |
| 5,891,095 A | 4/1999 | Eggers et al. | | 6,091,995 A | 7/2000 | Ingle et al. |
| 5,891,141 A | 4/1999 | Rydell | | 6,093,186 A | 7/2000 | Goble |
| 5,891,142 A | 4/1999 | Eggers et al. | | 6,095,149 A | 8/2000 | Sharkey et al. |
| 5,893,848 A | 4/1999 | Negus et al. | | 6,096,037 A | 8/2000 | Mulier et al. |
| 5,895,355 A | 4/1999 | Schaer | | 6,099,514 A | 8/2000 | Sharkey et al. |
| 5,895,417 A | 4/1999 | Pomeranz et al. | | 6,102,046 A | 8/2000 | Weinstein et al. |
| 5,897,553 A | 4/1999 | Mulier et al. | | 6,105,581 A | 8/2000 | Eggers et al. |
| 5,902,272 A | 5/1999 | Eggers et al. | | 6,109,268 A | 8/2000 | Thapliyal et al. |
| 5,902,328 A | 5/1999 | LaFontaine et al. | | 6,113,596 A | 9/2000 | Hooven et al. |
| 5,904,711 A | 5/1999 | Flom et al. | | 6,113,597 A | 9/2000 | Eggers et al. |
| 5,906,613 A | 5/1999 | Mulier et al. | | 6,117,109 A | 9/2000 | Eggers et al. |
| 5,913,854 A | 6/1999 | Maguire et al. | | 6,122,549 A | 9/2000 | Sharkey et al. |
| 5,913,856 A | 6/1999 | Chia et al. | | H1904 H | 10/2000 | Yates et al. |
| 5,919,191 A | 7/1999 | Lennox et al. | | 6,126,682 A | 10/2000 | Sharkey et al. |
| 5,919,219 A | 7/1999 | Knowlton | | 6,135,999 A * | 10/2000 | Fanton et al. .............. 606/45 |
| 5,921,982 A | 7/1999 | Lesh et al. | | 6,141,576 A | 10/2000 | Littmann et al. |
| 5,921,983 A | 7/1999 | Shannon, Jr. | | 6,142,992 A | 11/2000 | Cheng et al. |
| 5,925,045 A * | 7/1999 | Reimels et al. .............. 606/48 | | 6,149,620 A | 11/2000 | Baker et al. |
| 5,935,123 A | 8/1999 | Edwards et al. | | 6,159,194 A | 12/2000 | Eggers et al. |
| 5,948,011 A | 9/1999 | Knowlton | | 6,159,208 A | 12/2000 | Hovda et al. |
| 5,951,549 A | 9/1999 | Richardson et al. | | 6,165,169 A | 12/2000 | Panescu et al. |
| 5,954,716 A | 9/1999 | Sharkey et al. | | 6,165,175 A | 12/2000 | Wampler et al. |
| 5,957,919 A | 9/1999 | Laufer | | 6,168,594 B1 | 1/2001 | LaFontaine et al. |
| 5,964,755 A | 10/1999 | Edwards | | 6,171,275 B1 | 1/2001 | Webster, Jr. |
| 5,971,983 A | 10/1999 | Lesh | | 6,174,308 B1 | 1/2001 | Goble et al. |
| 5,976,128 A | 11/1999 | Schilling et al. | | 6,174,309 B1 | 1/2001 | Wrublewski et al. |
| 5,980,504 A | 11/1999 | Sharkey et al. | | 6,176,857 B1 | 1/2001 | Ashley |
| 5,980,516 A | 11/1999 | Mulier et al. | | 6,179,824 B1 | 1/2001 | Eggers et al. |
| 5,989,248 A | 11/1999 | Tu et al. | | 6,179,836 B1 | 1/2001 | Eggers et al. |
| 5,992,418 A | 11/1999 | de la Rama et al. | | 6,183,469 B1 | 2/2001 | Thapliyal et al. |
| 5,993,412 A | 11/1999 | Deily et al. | | 6,190,381 B1 | 2/2001 | Olsen et al. |
| 6,003,517 A | 12/1999 | Sheffield et al. | | 6,190,384 B1 | 2/2001 | Ouchi |
| 6,004,316 A | 12/1999 | Laufer | | 6,193,715 B1 | 2/2001 | Wrublewski et al. |
| 6,004,319 A | 12/1999 | Goble et al. | | 6,193,716 B1 | 2/2001 | Shannon, Jr. |
| 6,007,570 A | 12/1999 | Sharkey et al. | | 6,203,542 B1 | 3/2001 | Ellsberry et al. |
| 6,010,500 A | 1/2000 | Sherman et al. | | 6,210,402 B1 | 4/2001 | Olsen et al. |
| 6,015,391 A | 1/2000 | Rishton et al. | | 6,210,410 B1 | 4/2001 | Farin et al. |
| 6,015,407 A | 1/2000 | Rieb et al. | | 6,210,411 B1 | 4/2001 | Hofmann et al. |
| 6,016,809 A | 1/2000 | Mulier et al. | | 6,212,426 B1 | 4/2001 | Swanson |
| 6,017,338 A | 1/2000 | Brucker et al. | | 6,216,704 B1 | 4/2001 | Ingle et al. |
| 6,018,676 A | 1/2000 | Davis et al. | | 6,217,576 B1 | 4/2001 | Tu et al. |
| 6,019,757 A | 2/2000 | Scheldrup | | 6,221,039 B1 | 4/2001 | Durgin et al. |
| 6,024,733 A | 2/2000 | Eggers et al. | | 6,221,069 B1 | 4/2001 | Daikuzono |
| 6,027,501 A | 2/2000 | Goble et al. | | 6,224,592 B1 | 5/2001 | Eggers et al. |
| 6,030,379 A | 2/2000 | Panescu et al. | | 6,224,593 B1 | 5/2001 | Ryan et al. |
| 6,032,077 A | 2/2000 | Pomeranz | | 6,226,554 B1 | 5/2001 | Tu et al. |
| 6,032,674 A | 3/2000 | Eggers et al. | | 6,228,078 B1 | 5/2001 | Eggers et al. |
| 6,033,398 A | 3/2000 | Farley et al. | | 6,228,082 B1 | 5/2001 | Baker et al. |
| 6,035,238 A | 3/2000 | Ingle et al. | | 6,231,591 B1 | 5/2001 | Desai |
| 6,036,687 A | 3/2000 | Laufer et al. | | 6,235,020 B1 | 5/2001 | Cheng et al. |
| 6,045,532 A | 4/2000 | Eggers et al. | | 6,236,891 B1 | 5/2001 | Ingle et al. |
| 6,047,700 A | 4/2000 | Eggers et al. | | 6,238,387 B1 | 5/2001 | Miller, III |

| | | |
|---|---|---|
| 6,238,391 B1 | 5/2001 | Olsen et al. |
| 6,238,393 B1 | 5/2001 | Mulier et al. |
| 6,241,753 B1 | 6/2001 | Knowlton |
| 6,241,754 B1 | 6/2001 | Swanson et al. |
| 6,251,110 B1 | 6/2001 | Wampler |
| 6,254,600 B1 | 7/2001 | Willink et al. |
| 6,258,086 B1 | 7/2001 | Ashley et al. |
| 6,258,087 B1 | 7/2001 | Edwards et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,654 B1 | 7/2001 | Swartz et al. |
| 6,266,551 B1 | 7/2001 | Osadchy et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,283,988 B1 | 9/2001 | Laufer et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,293,945 B1 | 9/2001 | Parins et al. |
| 6,296,636 B1 | 10/2001 | Cheng et al. |
| 6,296,638 B1 | 10/2001 | Davison et al. |
| 6,296,640 B1 | 10/2001 | Wampler et al. |
| 6,299,633 B1 | 10/2001 | Laufer |
| 6,302,903 B1 | 10/2001 | Mulier et al. |
| 6,306,134 B1 | 10/2001 | Goble et al. |
| 6,309,387 B1 | 10/2001 | Eggers et al. |
| 6,311,090 B1 | 10/2001 | Knowlton |
| 6,312,408 B1 | 11/2001 | Eggers et al. |
| 6,312,430 B1 | 11/2001 | Wilson et al. |
| 6,315,777 B1 | 11/2001 | Comben |
| 6,322,549 B1 | 11/2001 | Eggers et al. |
| 6,322,559 B1 | 11/2001 | Daulton et al. |
| 6,327,505 B1 | 12/2001 | Medhkour et al. |
| 6,328,735 B1 | 12/2001 | Curley et al. |
| 6,328,736 B1 | 12/2001 | Mulier et al. |
| 6,336,926 B1 | 1/2002 | Goble |
| 6,350,262 B1 | 2/2002 | Ashley |
| 6,350,276 B1 | 2/2002 | Knowlton |
| 6,352,533 B1 | 3/2002 | Ellman et al. |
| 6,355,032 B1 | 3/2002 | Hovda et al. |
| 6,358,245 B1 | 3/2002 | Edwards et al. |
| 6,358,248 B1 | 3/2002 | Mulier et al. |
| 6,363,937 B1 | 4/2002 | Hovda et al. |
| 6,371,956 B1 | 4/2002 | Wilson et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,402,742 B1 | 6/2002 | Blewett et al. |
| 6,409,722 B1 | 6/2002 | Hoey et al. |
| 6,409,723 B1 | 6/2002 | Edwards |
| H2037 H | 7/2002 | Yates et al. |
| 6,416,507 B1 | 7/2002 | Eggers et al. |
| 6,416,508 B1 | 7/2002 | Eggers et al. |
| 6,419,509 B2 | 7/2002 | Cho |
| 6,425,877 B1 | 7/2002 | Edwards |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,451,017 B1 | 9/2002 | Moutafis et al. |
| 6,458,123 B1 | 10/2002 | Brucker et al. |
| 6,458,130 B1 | 10/2002 | Frazier et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,275 B1 | 10/2002 | Wampler et al. |
| 6,471,698 B1 | 10/2002 | Edwards et al. |
| 6,475,216 B2 | 11/2002 | Mulier et al. |
| 6,478,793 B1 | 11/2002 | Cosman et al. |
| 6,482,202 B1 | 11/2002 | Goble et al. |
| 6,485,490 B2 | 11/2002 | Wampler et al. |
| 6,488,680 B1 | 12/2002 | Francischelli et al. |
| 6,493,589 B1 | 12/2002 | Medhkour et al. |
| 6,494,902 B2 | 12/2002 | Hoey et al. |
| 6,497,704 B2 | 12/2002 | Ein-Gal |
| 6,497,705 B2 | 12/2002 | Comben |
| 6,506,189 B1 | 1/2003 | Rittman, III et al. |
| 6,508,815 B1 | 1/2003 | Strul et al. |
| 6,517,536 B2 | 2/2003 | Hooven et al. |
| 6,526,320 B2 | 2/2003 | Mitchell |
| 6,537,248 B2 | 3/2003 | Mulier et al. |
| 6,537,272 B2 | 3/2003 | Christopherson et al. |
| 6,539,265 B2 | 3/2003 | Medhkour et al. |
| 6,558,379 B1 | 5/2003 | Batchelor et al. |
| 6,558,385 B1 | 5/2003 | McClurken et al. |
| 6,575,969 B1 | 6/2003 | Rittman, III et al. |
| 6,577,902 B1 | 6/2003 | Laufer et al. |
| 6,579,288 B1 | 6/2003 | Swanson et al. |
| 6,585,732 B2 | 7/2003 | Mulier et al. |
| 6,602,248 B1 | 8/2003 | Sharps et al. |
| 6,603,988 B2 | 8/2003 | Dowlatshahi |
| 6,610,060 B2 | 8/2003 | Mulier et al. |
| 6,613,048 B2 | 9/2003 | Mulier et al. |
| 6,623,515 B2 | 9/2003 | Mulier et al. |
| 6,626,899 B2 | 9/2003 | Houser et al. |
| 6,645,202 B1 | 11/2003 | Pless et al. |
| 6,666,862 B2 | 12/2003 | Jain et al. |
| 6,669,692 B1 | 12/2003 | Nelson et al. |
| 6,676,660 B2 | 1/2004 | Wampler et al. |
| 6,679,882 B1 | 1/2004 | Kornerup |
| 6,682,501 B1 | 1/2004 | Nelson et al. |
| 6,682,527 B2 | 1/2004 | Strul |
| 6,682,528 B2 | 1/2004 | Frazier et al. |
| 6,685,700 B2 | 2/2004 | Behl et al. |
| 6,685,701 B2 | 2/2004 | Orszulak et al. |
| 6,685,704 B2 | 2/2004 | Greep |
| 6,689,129 B2 | 2/2004 | Baker |
| 6,689,131 B2 | 2/2004 | McClurken |
| 6,692,489 B1 | 2/2004 | Heim et al. |
| 6,694,984 B2 | 2/2004 | Habib |
| 6,695,837 B2 | 2/2004 | Howell |
| 6,695,840 B2 | 2/2004 | Schulze |
| 6,699,240 B2 | 3/2004 | Francischelli |
| 6,699,242 B2 | 3/2004 | Heggeness |
| 6,699,244 B2 | 3/2004 | Carranza et al. |
| 6,699,268 B2 | 3/2004 | Kordis et al. |
| 6,702,810 B2 | 3/2004 | McClurken et al. |
| 6,702,812 B2 | 3/2004 | Cosmescu |
| 6,706,039 B2 | 3/2004 | Mulier et al. |
| 6,712,074 B2 | 3/2004 | Edwards et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,716,211 B2 | 4/2004 | Mulier et al. |
| 6,719,754 B2 | 4/2004 | Underwood et al. |
| 6,723,094 B1 | 4/2004 | Desinger |
| 6,726,683 B1 | 4/2004 | Shaw |
| 6,726,684 B1 | 4/2004 | Woloszko et al. |
| 6,726,686 B2 | 4/2004 | Buysse et al. |
| 6,730,081 B1 | 5/2004 | Desai |
| 6,733,496 B2 | 5/2004 | Sharkey et al. |
| 6,733,498 B2 | 5/2004 | Paton et al. |
| 6,733,501 B2 | 5/2004 | Levine |
| 6,736,810 B2 | 5/2004 | Hoey et al. |
| 6,740,058 B2 | 5/2004 | Lal et al. |
| 6,740,079 B1 | 5/2004 | Eggers et al. |
| 6,740,082 B2 | 5/2004 | Shadduck |
| 6,740,084 B2 | 5/2004 | Ryan |
| 6,740,102 B2 | 5/2004 | Hess et al. |
| 6,743,197 B1 | 6/2004 | Edwards |

| | | |
|---|---|---|
| 6,743,229 B2 | 6/2004 | Buysse et al. |
| 6,743,230 B2 | 6/2004 | Lutze et al. |
| 6,746,447 B2 | 6/2004 | Davison et al. |
| 6,755,825 B2 | 6/2004 | Shoenman et al. |
| 6,755,827 B2 | 6/2004 | Mulier et al. |
| 6,757,565 B2 | 6/2004 | Sharkey et al. |
| 6,758,846 B2 | 7/2004 | Goble et al. |
| 6,761,718 B2 | 7/2004 | Madsen |
| 6,764,487 B2 | 7/2004 | Mulier et al. |
| 6,766,817 B2 | 7/2004 | da Silva |
| 6,770,070 B1 | 8/2004 | Balbierz |
| 6,770,071 B2 | 8/2004 | Woloszko et al. |
| 6,770,072 B1 | 8/2004 | Truckai et al. |
| 6,772,012 B2 | 8/2004 | Ricart et al. |
| 6,772,013 B1 | 8/2004 | Ingle et al. |
| 6,775,575 B2 | 8/2004 | Bommannan et al. |
| 6,776,780 B2 | 8/2004 | Mulier et al. |
| 6,780,177 B2 | 8/2004 | Shafirstein et al. |
| 6,780,180 B1 | 8/2004 | Goble et al. |
| 6,786,906 B1 | 9/2004 | Cobb |
| 6,796,981 B2 | 9/2004 | Wham et al. |
| 6,800,077 B1 | 10/2004 | Mucko et al. |
| 6,802,842 B2 | 10/2004 | Ellman et al. |
| 6,802,843 B2 | 10/2004 | Truckai et al. |
| 6,808,525 B2 | 10/2004 | Latterell et al. |
| 6,813,520 B2 | 11/2004 | Truckai et al. |
| 6,814,714 B1 | 11/2004 | Novak et al. |
| 6,814,731 B2 | 11/2004 | Swanson |
| 6,821,273 B2 | 11/2004 | Mollenauer |
| 6,827,713 B2 | 12/2004 | Bek et al. |
| 6,827,725 B2 | 12/2004 | Batchelor et al. |
| 6,832,997 B2 | 12/2004 | Uchida et al. |
| 6,835,195 B2 | 12/2004 | Schulze et al. |
| 6,836,688 B2 | 12/2004 | Ingle et al. |
| 6,843,789 B2 | 1/2005 | Goble |
| 6,845,264 B1 | 1/2005 | Skladnev et al. |
| 6,849,073 B2 | 2/2005 | Hoey et al. |
| 6,855,145 B2 | 2/2005 | Ciarrocca |
| 6,858,028 B2 | 2/2005 | Mulier et al. |
| 6,860,882 B2 | 3/2005 | Battles et al. |
| 6,863,669 B2 | 3/2005 | Spitzer |
| 6,864,686 B2 | 3/2005 | Novak et al. |
| 6,881,214 B2 | 4/2005 | Cosman et al. |
| 6,882,885 B2 | 4/2005 | Levy, Jr. et al. |
| 6,887,237 B2 | 5/2005 | McGaffigan |
| 6,887,240 B1 | 5/2005 | Lands et al. |
| 6,893,435 B2 | 5/2005 | Goble |
| 6,893,440 B2 | 5/2005 | Durgin et al. |
| 6,896,672 B1 | 5/2005 | Eggers et al. |
| 6,896,674 B1 | 5/2005 | Woloszko et al. |
| 6,899,712 B2 | 5/2005 | Moutafis et al. |
| 6,905,497 B2 | 6/2005 | Truckai et al. |
| 6,905,499 B1 | 6/2005 | Mucko et al. |
| 6,911,019 B2 | 6/2005 | Mulier et al. |
| 6,915,806 B2 | 7/2005 | Pacek et al. |
| 6,918,404 B2 | 7/2005 | Dias da Silva |
| 6,921,398 B2 | 7/2005 | Carmel et al. |
| 6,921,399 B2 | 7/2005 | Carmel et al. |
| 6,923,803 B2 | 8/2005 | Goble |
| 6,923,805 B1 | 8/2005 | LaFontaine et al. |
| 6,926,706 B1 | 8/2005 | Sealfon |
| 6,926,716 B2 | 8/2005 | Baker et al. |
| 6,926,717 B1 | 8/2005 | Garito et al. |
| 6,929,640 B1 | 8/2005 | Underwood et al. |
| 6,929,641 B2 | 8/2005 | Goble et al. |
| 6,929,642 B2 | 8/2005 | Xiao et al. |
| 6,929,644 B2 | 8/2005 | Truckai et al. |
| 6,929,645 B2 | 8/2005 | Battles et al. |
| 6,932,810 B2 | 8/2005 | Ryan |
| 6,932,815 B2 | 8/2005 | Sutter |
| 6,942,661 B2 | 9/2005 | Swanson |
| 6,942,662 B2 * | 9/2005 | Goble et al. .......... 606/48 |
| 6,949,096 B2 | 9/2005 | Davison et al. |
| 6,949,098 B2 | 9/2005 | Mulier et al. |
| 6,951,559 B1 | 10/2005 | Greep |
| 6,953,461 B2 | 10/2005 | McClurken et al. |
| 6,960,204 B2 | 11/2005 | Eggers et al. |
| 6,960,207 B2 | 11/2005 | Vanney et al. |
| 6,960,210 B2 | 11/2005 | Lands et al. |
| 6,962,589 B2 | 11/2005 | Mulier et al. |
| 6,964,274 B1 | 11/2005 | Ryan et al. |
| 6,964,661 B2 | 11/2005 | Rioux et al. |
| 6,966,907 B2 | 11/2005 | Goble |
| 6,966,909 B2 | 11/2005 | Marshall et al. |
| 6,971,394 B2 | 12/2005 | Sliwa, Jr. et al. |
| 6,974,452 B1 | 12/2005 | Gille et al. |
| 6,974,453 B2 | 12/2005 | Woloszko et al. |
| 6,979,332 B2 | 12/2005 | Adams |
| 6,984,231 B2 | 1/2006 | Goble et al. |
| 6,986,769 B2 | 1/2006 | Nelson et al. |
| 6,991,631 B2 | 1/2006 | Woloszko et al. |
| 7,001,380 B2 | 2/2006 | Goble |
| 7,001,382 B2 | 2/2006 | Gallo, Sr. |
| 7,004,941 B2 | 2/2006 | Tvinnereim et al. |
| 7,004,942 B2 | 2/2006 | Laird et al. |
| 7,008,419 B2 | 3/2006 | Shadduck |
| 7,008,421 B2 | 3/2006 | Daniel et al. |
| 7,033,348 B2 | 4/2006 | Alfano et al. |
| 7,033,356 B2 | 4/2006 | Latterell et al. |
| 7,041,096 B2 | 5/2006 | Malis et al. |
| 7,041,101 B2 | 5/2006 | Eggers |
| 7,041,102 B2 | 5/2006 | Truckai et al. |
| 7,052,494 B2 | 5/2006 | Goble et al. |
| 7,060,064 B2 | 6/2006 | Allen et al. |
| 7,063,670 B2 | 6/2006 | Sampson et al. |
| 7,066,586 B2 | 6/2006 | da Silva |
| 7,066,932 B1 | 6/2006 | Morgan et al. |
| 7,066,936 B2 | 6/2006 | Ryan |
| 7,070,596 B1 | 7/2006 | Woloszko et al. |
| 7,070,604 B1 | 7/2006 | Garito et al. |
| 7,074,217 B2 | 7/2006 | Strul et al. |
| 7,074,219 B2 | 7/2006 | Levine et al. |
| 7,083,601 B1 | 8/2006 | Cosmescu |
| 7,087,051 B2 | 8/2006 | Bourne et al. |
| 7,087,053 B2 | 8/2006 | Vanney |
| 7,094,215 B2 | 8/2006 | Davison et al. |
| 7,101,387 B2 | 9/2006 | Garabedian et al. |
| 7,104,986 B2 | 9/2006 | Hovda et al. |
| 7,112,199 B2 | 9/2006 | Cosmescu |
| 7,115,139 B2 | 10/2006 | McClurken et al. |
| 7,125,406 B2 | 10/2006 | Given |
| 7,147,634 B2 | 12/2006 | Nesbitt |
| 7,147,635 B2 | 12/2006 | Ciarrocca |
| 7,147,637 B2 | 12/2006 | Goble |
| 7,147,638 B2 | 12/2006 | Chapman et al. |
| 7,150,746 B2 | 12/2006 | DeCesare et al. |
| 7,150,747 B1 | 12/2006 | McDonald et al. |
| 7,150,748 B2 | 12/2006 | Ebbutt et al. |
| 7,153,300 B2 | 12/2006 | Goble |
| 7,156,845 B2 | 1/2007 | Mulier et al. |
| 7,166,105 B2 | 1/2007 | Mulier et al. |
| 7,166,106 B2 | 1/2007 | Bartel et al. |
| 7,169,143 B2 | 1/2007 | Eggers et al. |
| 7,169,144 B2 | 1/2007 | Hoey et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |

| | | |
|---|---|---|
| 2001/0025178 A1 | 9/2001 | Mulier et al. |
| 2001/0032002 A1 | 10/2001 | McClurken et al. |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |
| 2002/0002393 A1 | 1/2002 | Mitchell |
| 2002/0010463 A1 | 1/2002 | Mulier et al. |
| 2002/0013582 A1 | 1/2002 | Mulier et al. |
| 2002/0016589 A1 | 2/2002 | Swartz et al. |
| 2002/0019628 A1 | 2/2002 | Comben |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0035387 A1 | 3/2002 | Mulier et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0062123 A1 | 5/2002 | McClurken et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel et al. |
| 2002/0151884 A1 | 10/2002 | Hoey et al. |
| 2002/0156511 A1 | 10/2002 | Habib |
| 2002/0161364 A1 | 10/2002 | Mulier et al. |
| 2002/0169446 A1 | 11/2002 | Mulier et al. |
| 2002/0177846 A1 | 11/2002 | Mulier et al. |
| 2002/0183733 A1 | 12/2002 | Mulier et al. |
| 2002/0188284 A1 | 12/2002 | To et al. |
| 2002/0193851 A1 | 12/2002 | Silverman et al. |
| 2002/0198524 A1 | 12/2002 | Mulier et al. |
| 2003/0004510 A1 | 1/2003 | Wham et al. |
| 2003/0014050 A1 | 1/2003 | Sharkey et al. |
| 2003/0032954 A1 | 2/2003 | Carranza et al. |
| 2003/0032955 A1 | 2/2003 | Mulier et al. |
| 2003/0073989 A1 | 4/2003 | Hoey et al. |
| 2003/0073993 A1 | 4/2003 | Ciarrocca |
| 2003/0114850 A1 | 6/2003 | McClurken et al. |
| 2003/0181902 A1 | 9/2003 | Mulier et al. |
| 2003/0204185 A1 | 10/2003 | Sherman et al. |
| 2003/0216733 A1 | 11/2003 | McClurken et al. |
| 2004/0015162 A1 | 1/2004 | McGaffigan |
| 2004/0015163 A1 | 1/2004 | Buysse et al. |
| 2004/0015215 A1 | 1/2004 | Fredricks et al. |
| 2004/0015216 A1 | 1/2004 | DeSisto |
| 2004/0015218 A1 | 1/2004 | Finch et al. |
| 2004/0019350 A1 | 1/2004 | O'Brien et al. |
| 2004/0024395 A1 | 2/2004 | Ellman et al. |
| 2004/0024396 A1 | 2/2004 | Eggers |
| 2004/0024398 A1 | 2/2004 | Hovda et al. |
| 2004/0024399 A1 | 2/2004 | Sharps et al. |
| 2004/0030327 A1 | 2/2004 | Golan |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030333 A1 | 2/2004 | Goble |
| 2004/0034340 A1 | 2/2004 | Biscup |
| 2004/0034346 A1 | 2/2004 | Stern et al. |
| 2004/0034349 A1 | 2/2004 | Kirwan, Jr. et al. |
| 2004/0034400 A1 | 2/2004 | Ingle et al. |
| 2004/0039429 A1 | 2/2004 | Daniel et al. |
| 2004/0044341 A1 | 3/2004 | Truckai et al. |
| 2004/0054363 A1 | 3/2004 | Vaska et al. |
| 2004/0054365 A1 | 3/2004 | Goble |
| 2004/0054366 A1 | 3/2004 | Davison et al. |
| 2004/0054369 A1 | 3/2004 | Nelson et al. |
| 2004/0054370 A1 | 3/2004 | Given |
| 2004/0059328 A1 | 3/2004 | Daniel et al. |
| 2004/0059363 A1 | 3/2004 | Alvarez et al. |
| 2004/0064023 A1 | 4/2004 | Ryan et al. |
| 2004/0064137 A1 | 4/2004 | Pellegrino et al. |
| 2004/0068306 A1 | 4/2004 | Shadduck |
| 2004/0068307 A1 | 4/2004 | Goble |
| 2004/0073205 A1 | 4/2004 | Treat et al. |
| 2004/0073208 A1 | 4/2004 | Sutter |
| 2004/0078034 A1 | 4/2004 | Acker et al. |
| 2004/0078037 A1 | 4/2004 | Batchelor et al. |
| 2004/0078038 A1 | 4/2004 | Desinger et al. |
| 2004/0082946 A1 | 4/2004 | Malis et al. |
| 2004/0082952 A1 | 4/2004 | Dycus et al. |
| 2004/0087937 A1 | 5/2004 | Eggers et al. |
| 2004/0087939 A1 | 5/2004 | Eggers et al. |
| 2004/0087940 A1 | 5/2004 | Jahns et al. |
| 2004/0087943 A1 | 5/2004 | Dycus et al. |
| 2004/0088029 A1 | 5/2004 | Yamamoto |
| 2004/0092925 A1 | 5/2004 | Rizoiu et al. |
| 2004/0092926 A1 | 5/2004 | Hoey et al. |
| 2004/0097919 A1 | 5/2004 | Wellman et al. |
| 2004/0102770 A1 | 5/2004 | Goble |
| 2004/0102824 A1 | 5/2004 | Sharkey et al. |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0122420 A1 | 6/2004 | Amoah |
| 2004/0122423 A1 | 6/2004 | Dycus et al. |
| 2004/0122494 A1 | 6/2004 | Eggers et al. |
| 2004/0138654 A1 | 7/2004 | Goble |
| 2004/0138655 A1 | 7/2004 | McClurken et al. |
| 2004/0138657 A1 | 7/2004 | Bourne et al. |
| 2004/0143257 A1 | 7/2004 | Fuimaono |
| 2004/0143258 A1 | 7/2004 | Fuimaono |
| 2004/0143259 A1 | 7/2004 | Mulier et al. |
| 2004/0143263 A1 | 7/2004 | Schechter et al. |
| 2004/0147902 A1 | 7/2004 | McGuckin, Jr. et al. |
| 2004/0147916 A1 | 7/2004 | Baker |
| 2004/0147922 A1 | 7/2004 | Keppel |
| 2004/0147925 A1 | 7/2004 | Buysse et al. |
| 2004/0162552 A1 | 8/2004 | McClurken |
| 2004/0162554 A1 | 8/2004 | Lee et al. |
| 2004/0162557 A1 | 8/2004 | Tetzlaff et al. |
| 2004/0162572 A1 | 8/2004 | Sauer |
| 2004/0167508 A1 | 8/2004 | Wham et al. |
| 2004/0172111 A1 | 9/2004 | Hijii et al. |
| 2004/0176760 A1 | 9/2004 | Qiu |
| 2004/0176761 A1 | 9/2004 | Desinger |
| 2004/0176762 A1 | 9/2004 | Lawes et al. |
| 2004/0181219 A1 | 9/2004 | Goble et al. |
| 2004/0181250 A1 | 9/2004 | Adams et al. |
| 2004/0186469 A1 | 9/2004 | Woloszko et al. |
| 2004/0186470 A1 | 9/2004 | Goble et al. |
| 2004/0186535 A1 | 9/2004 | Knowlton |
| 2004/0193148 A1 | 9/2004 | Wham et al. |
| 2004/0193150 A1 | 9/2004 | Sharkey et al. |
| 2004/0193152 A1 | 9/2004 | Sutton et al. |
| 2004/0193211 A1 | 9/2004 | Voegele et al. |
| 2004/0199156 A1 | 10/2004 | Rioux et al. |
| 2004/0199160 A1 | 10/2004 | Slater |
| 2004/0206365 A1 | 10/2004 | Knowlton |
| 2004/0210213 A1 | 10/2004 | Fuimaono et al. |
| 2004/0210214 A1 | 10/2004 | Knowlton |
| 2004/0215181 A1 | 10/2004 | Christopherson et al. |
| 2004/0215182 A1 | 10/2004 | Lee |
| 2004/0215183 A1 | 10/2004 | Hoey et al. |
| 2004/0215184 A1 | 10/2004 | Eggers et al. |

| | | | | | | |
|---|---|---|---|---|---|---|
| 2004/0215185 A1 | 10/2004 | Truckai et al. | | 2005/0171533 A1 | 8/2005 | Latterell et al. |
| 2004/0215188 A1 | 10/2004 | Mulier et al. | | 2005/0171534 A1 | 8/2005 | Habib |
| 2004/0215235 A1 | 10/2004 | Jackson et al. | | 2005/0171583 A1 | 8/2005 | Mosher et al. |
| 2004/0215296 A1 | 10/2004 | Ganz et al. | | 2005/0177150 A1 | 8/2005 | Amoah et al. |
| 2004/0220561 A1 | 11/2004 | Kirwan, Jr. et al. | | 2005/0177209 A1 | 8/2005 | Leung et al. |
| 2004/0220562 A1 | 11/2004 | Garabedian et al. | | 2005/0187543 A1 | 8/2005 | Underwood et al. |
| 2004/0225288 A1 | 11/2004 | Buysse et al. | | 2005/0187599 A1 | 8/2005 | Sharkey et al. |
| 2004/0230190 A1 | 11/2004 | Dahla et al. | | 2005/0203503 A1 | 9/2005 | Edwards et al. |
| 2004/0236322 A1 | 11/2004 | Mulier et al. | | 2005/0203504 A1 | 9/2005 | Wham et al. |
| 2004/0236324 A1 | 11/2004 | Muller et al. | | 2005/0209591 A1 | 9/2005 | Sutter |
| 2004/0243125 A1 | 12/2004 | Dycus et al. | | 2005/0209621 A1 | 9/2005 | Gordon et al. |
| 2004/0243163 A1 | 12/2004 | Casiano et al. | | 2005/0222602 A1 | 10/2005 | Sutter et al. |
| 2004/0249371 A1 | 12/2004 | Dycus et al. | | 2005/0222611 A1 | 10/2005 | Weitkamp |
| 2004/0249374 A1 | 12/2004 | Tetzlaff et al. | | 2005/0228372 A1 | 10/2005 | Truckai et al. |
| 2004/0249425 A1 | 12/2004 | Roy et al. | | 2005/0245918 A1 | 11/2005 | Sliwa et al. |
| 2004/0260279 A1 | 12/2004 | Goble et al. | | 2005/0245921 A1 | 11/2005 | Strul et al. |
| 2004/0260280 A1 | 12/2004 | Sartor | | 2005/0245922 A1 | 11/2005 | Goble |
| 2004/0260368 A1 | 12/2004 | Ingle et al. | | 2005/0245923 A1 | 11/2005 | Christopherson et al. |
| 2005/0010205 A1 | 1/2005 | Hovda et al. | | 2005/0250477 A1 | 11/2005 | Eastwood et al. |
| 2005/0010212 A1 | 1/2005 | McClurken et al. | | 2005/0251128 A1 | 11/2005 | Amoah |
| 2005/0015085 A1 | 1/2005 | McClurken et al. | | 2005/0251134 A1 | 11/2005 | Woloszko et al. |
| 2005/0015086 A1 | 1/2005 | Platt | | 2005/0256519 A1 | 11/2005 | Goble et al. |
| 2005/0015130 A1 | 1/2005 | Gill | | 2005/0261676 A1 | 11/2005 | Hall et al. |
| 2005/0021025 A1 | 1/2005 | Buysse et al. | | 2005/0261677 A1 | 11/2005 | Hall et al. |
| 2005/0021026 A1 | 1/2005 | Baily | | 2005/0267465 A1 | 12/2005 | Hillier et al. |
| 2005/0021027 A1 | 1/2005 | Shields et al. | | 2005/0267467 A1 | 12/2005 | Paul et al. |
| 2005/0033278 A1 | 2/2005 | McClurken et al. | | 2005/0267468 A1 | 12/2005 | Truckai et al. |
| 2005/0033292 A1 | 2/2005 | Teitelbaum et al. | | 2005/0267469 A1 | 12/2005 | Blocher |
| 2005/0038471 A1 | 2/2005 | Chan et al. | | 2005/0273092 A1 | 12/2005 | G. et al. |
| 2005/0043728 A1 | 2/2005 | Ciarrocca | | 2005/0273097 A1 | 12/2005 | Ryan |
| 2005/0049583 A1 | 3/2005 | Swanson | | 2005/0277915 A1 | 12/2005 | DeCesare et al. |
| 2005/0049586 A1 | 3/2005 | Daniel et al. | | 2005/0277916 A1 | 12/2005 | DeCesare et al. |
| 2005/0055019 A1 | 3/2005 | Skarda | | 2005/0277917 A1 | 12/2005 | Garito et al. |
| 2005/0055020 A1 | 3/2005 | Skarda | | 2005/0283147 A1 | 12/2005 | Yachi |
| 2005/0059966 A1 | 3/2005 | McClurken et al. | | 2005/0283148 A1 | 12/2005 | Janssen et al. |
| 2005/0070888 A1 | 3/2005 | Dimatteo et al. | | 2005/0283149 A1 | 12/2005 | Thorne et al. |
| 2005/0070891 A1 | 3/2005 | DeSisto | | 2005/0283150 A1 | 12/2005 | Moutafis et al. |
| 2005/0070894 A1 | 3/2005 | McClurken | | 2005/0283151 A1 | 12/2005 | Ebbutt et al. |
| 2005/0070896 A1 | 3/2005 | Daniel et al. | | 2005/0288661 A1 | 12/2005 | Sauvageau et al. |
| 2005/0080410 A1 | 4/2005 | Rioux et al. | | 2005/0288665 A1 | 12/2005 | Woloszko |
| 2005/0080413 A1 | 4/2005 | Canady | | 2006/0004356 A1 | 1/2006 | Bilski et al. |
| 2005/0085804 A1 | 4/2005 | McGaffigan | | 2006/0009760 A1 | 1/2006 | Mulier et al. |
| 2005/0085809 A1 | 4/2005 | Mucko et al. | | 2006/0009762 A1 | 1/2006 | Whayne |
| 2005/0085880 A1 | 4/2005 | Truckai et al. | | 2006/0015097 A1 | 1/2006 | Mulier et al. |
| 2005/0090816 A1 | 4/2005 | McClurken et al. | | 2006/0020265 A1 | 1/2006 | Ryan |
| 2005/0090819 A1 | 4/2005 | Goble | | 2006/0025765 A1 | 2/2006 | Landman et al. |
| 2005/0096649 A1 | 5/2005 | Adams | | 2006/0025766 A1 | 2/2006 | Heinrich et al. |
| 2005/0096651 A1 | 5/2005 | Truckai et al. | | 2006/0030912 A1 | 2/2006 | Eggers et al. |
| 2005/0101951 A1 | 5/2005 | Wham et al. | | 2006/0036235 A1 | 2/2006 | Swoyer et al. |
| 2005/0101952 A1 | 5/2005 | Lands et al. | | 2006/0036237 A1 | 2/2006 | Davison et al. |
| 2005/0101965 A1 | 5/2005 | Ryan | | 2006/0036239 A1 | 2/2006 | Canady |
| 2005/0107778 A1 | 5/2005 | Rioux et al. | | 2006/0041254 A1 | 2/2006 | Francischelli et al. |
| 2005/0107779 A1 | 5/2005 | Ellman et al. | | 2006/0041255 A1 | 2/2006 | Eggers et al. |
| 2005/0107784 A1 | 5/2005 | Moses et al. | | 2006/0047275 A1 | 3/2006 | Goble |
| 2005/0107786 A1 | 5/2005 | Canady | | 2006/0047280 A1 | 3/2006 | Goble et al. |
| 2005/0113820 A1 | 5/2005 | Goble et al. | | 2006/0047331 A1 | 3/2006 | Lax et al. |
| 2005/0113825 A1 | 5/2005 | Cosmescu | | 2006/0052770 A1 | 3/2006 | Mulier et al. |
| 2005/0124987 A1 | 6/2005 | Goble | | 2006/0064085 A1 | 3/2006 | Baker et al. |
| 2005/0130929 A1 | 6/2005 | Boyd | | 2006/0064101 A1 | 3/2006 | Arramon |
| 2005/0131402 A1 | 6/2005 | Ciarrocca et al. | | 2006/0074411 A1 | 4/2006 | Carmel et al. |
| 2005/0137590 A1 | 6/2005 | Lawes et al. | | 2006/0074414 A1 | 4/2006 | Mulier et al. |
| 2005/0137662 A1 | 6/2005 | Morris et al. | | 2006/0079872 A1 | 4/2006 | Eggleston |
| 2005/0143729 A1 | 6/2005 | Francischelli et al. | | 2006/0079888 A1 | 4/2006 | Mulier et al. |
| 2005/0154385 A1 | 7/2005 | Heim et al. | | 2006/0084968 A1 | 4/2006 | Truckai et al. |
| 2005/0154433 A1 | 7/2005 | Levy et al. | | 2006/0095026 A1 | 5/2006 | Ricart et al. |
| 2005/0159739 A1 | 7/2005 | Paul et al. | | 2006/0095031 A1 | 5/2006 | Ormsby |
| 2005/0159740 A1 | 7/2005 | Paul et al. | | 2006/0095034 A1 | 5/2006 | Garito et al. |
| 2005/0159778 A1 | 7/2005 | Heinrich et al. | | 2006/0095075 A1 | 5/2006 | Burkinshaw et al. |
| 2005/0159797 A1 | 7/2005 | Chandran et al. | | 2006/0095103 A1 | 5/2006 | Eggers et al. |
| 2005/0165444 A1 | 7/2005 | Hart et al. | | 2006/0100619 A1 | 5/2006 | McClurken et al. |
| 2005/0171524 A1 | 8/2005 | Stern et al. | | 2006/0106376 A1 | 5/2006 | Godara et al. |
| 2005/0171526 A1 | 8/2005 | Rioux et al. | | 2006/0106379 A1 | 5/2006 | O'Brien et al. |
| 2005/0171532 A1 | 8/2005 | Ciarrocca | | 2006/0111705 A1 | 5/2006 | Janzen et al. |

| | | |
|---|---|---|
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |
| 2006/0241577 A1 | 10/2006 | Balbierz et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0247614 A1 | 11/2006 | Sampson et al. |
| 2006/0259025 A1 | 11/2006 | Dahla |
| 2006/0259031 A1 | 11/2006 | Carmel et al. |
| 2006/0259070 A1 | 11/2006 | Livneh |
| 2006/0264927 A1 | 11/2006 | Ryan |
| 2006/0264929 A1 | 11/2006 | Goble et al. |
| 2006/0264931 A1 | 11/2006 | Chapman et al. |
| 2006/0271033 A1 | 11/2006 | Ein-Gal |
| 2006/0271036 A1 | 11/2006 | Garabedian et al. |
| 2006/0271042 A1 | 11/2006 | Latterell et al. |
| 2006/0276783 A1 | 12/2006 | Cosmescu |
| 2006/0276785 A1 | 12/2006 | Asahara et al. |
| 2007/0000501 A1 | 1/2007 | Wert et al. |
| 2007/0010812 A1 | 1/2007 | Mittelstein et al. |
| 2007/0016182 A1 | 1/2007 | Lipson et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0071270 A1 | 3/2008 | Baker et al. |

FOREIGN PATENT DOCUMENTS

| | | |
|---|---|---|
| EP | 0 175 595 | 3/1986 |
| EP | 1 095 627 A1 | 5/2001 |
| FR | 2 235 669 | 1/1975 |
| JP | 57-117843 | 7/1982 |
| JP | 5-092009 | 4/1993 |
| JP | 7-124245 | 5/1995 |
| WO | WO 97/05829 A1 | 2/1997 |
| WO | WO 98/38932 A1 | 9/1998 |
| WO | WO 99/66850 A1 | 12/1999 |
| WO | WO 00/78240 A1 | 12/2000 |
| WO | WO 01/28444 A1 | 4/2001 |
| WO | WO 01/80757 A2 | 11/2001 |
| WO | WO 2005/122938 A1 | 12/2005 |
| WO | WO 2006/062916 A2 | 6/2006 |
| WO | WO 2006/062939 A2 | 6/2006 |

* cited by examiner

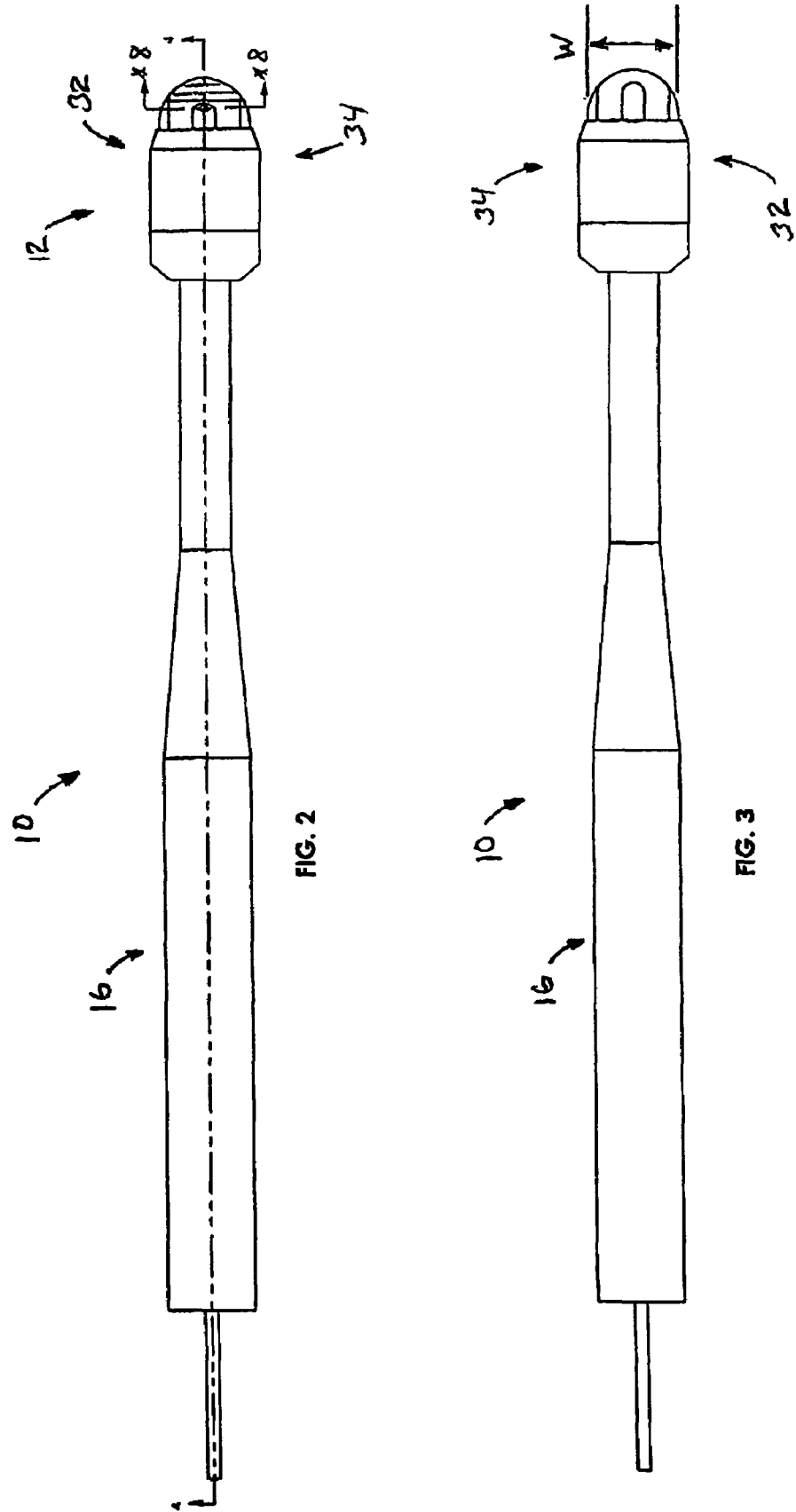

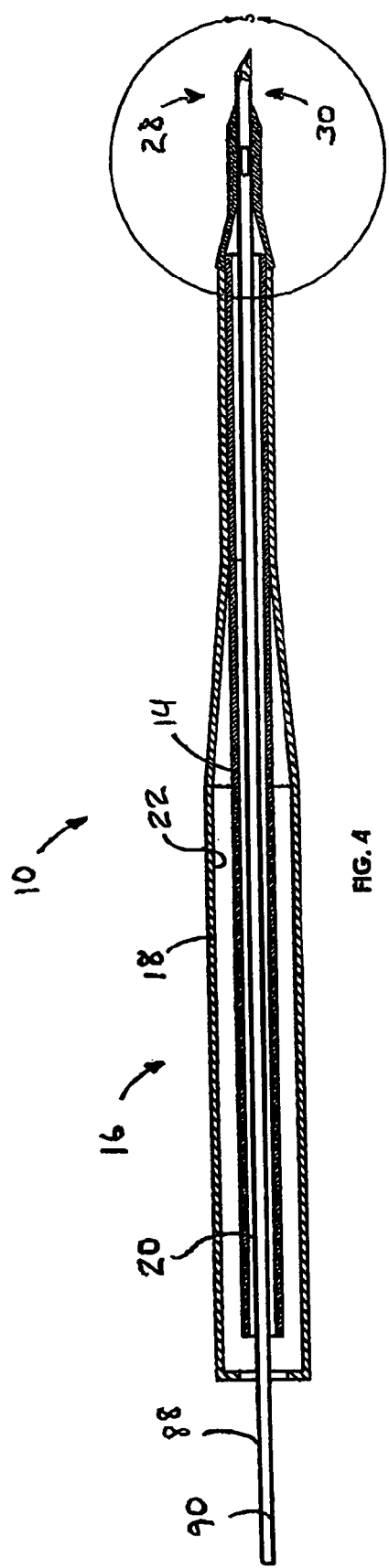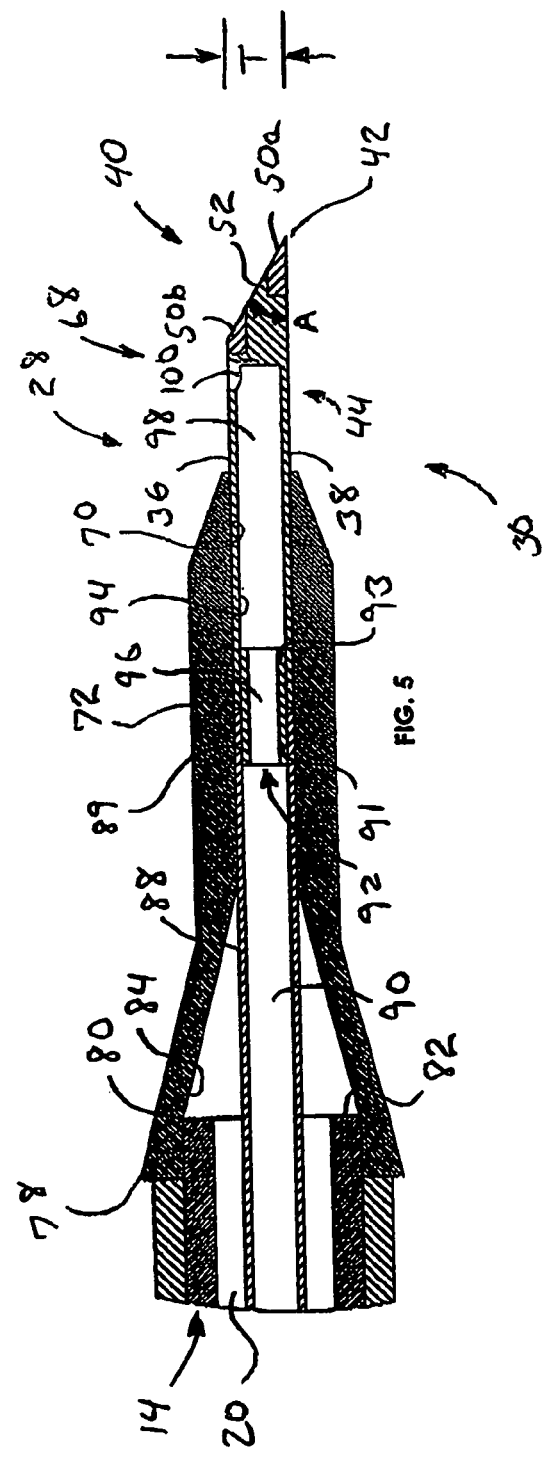

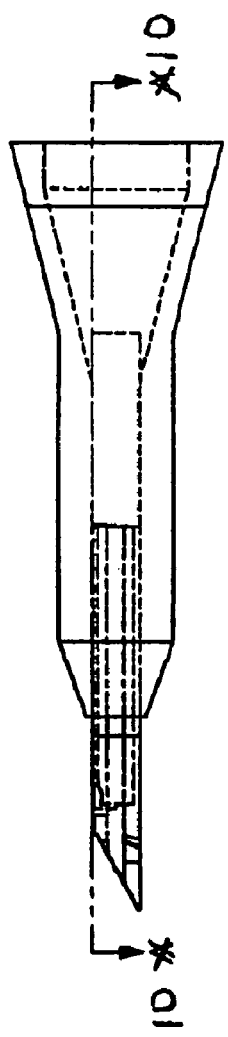
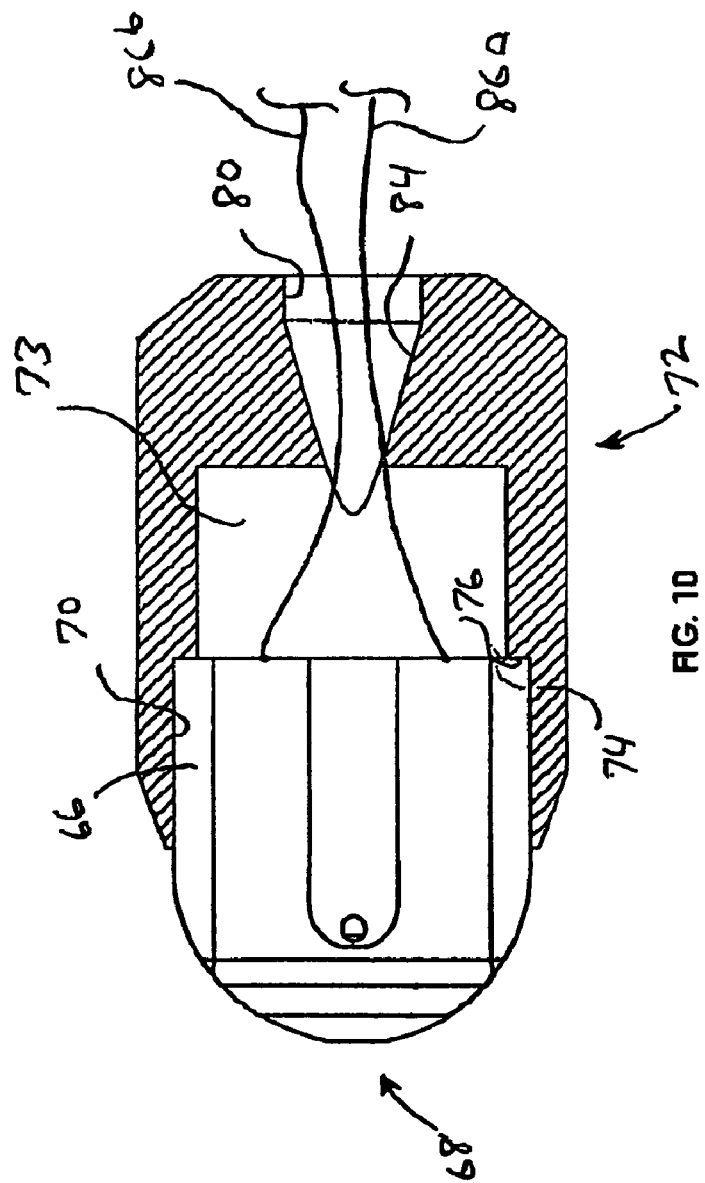
FIG. 9
FIG. 10

FLUID-ASSISTED MEDICAL DEVICES AND METHODS

FIELD

This invention relates generally to the field of medical devices and methods for use upon a body during surgery. More particularly, the invention relates to electrosurgical devices, systems and methods for use upon tissues of a human body during surgery, particularly open surgery.

BACKGROUND

The human spinal column is composed of bone vertebrae which support the upper body. Around and attached to the vertebrae are, among other things, various muscles which act on the vertebrae to affect movement of the upper body. While a vast majority of the population has a normally shaped spinal column, a portion of the population suffers from an abnormal curvature of the spinal column known as scoliosis.

Scoliosis is treated by fusing various vertebrae together along the curvature to straighten the spine column. During a fusion procedure, the surgeon first retracts the soft tissue connected to the vertebrae to be fused, and thereafter removes certain of the processes (bone projections) from the vertebrae. The vertebrae are then aligned to straighten the spinal column, and stabilized relative to one another by a steel rod which is attached to the vertebrae by numerous fastening techniques. The surgeon then places bone graphs across the exposed surfaces of adjoining vertebrae and restores the location of the soft tissue to cover the bone graphs and vertebrae. The graphs regenerate, grow into bone and fuse the vertebrae together, with the rod functioning as a temporary splint which stabilizes the spinal column while the bone fuses together over a period of months.

Fusion procedures to treat scoliosis generally take many hours. In some cases, the entire length of the spinal column is substantially exposed and the surgical procedure may take eight hours or more. Consequently, blood loss during the procedure can be significant. A great amount of this blood loss occurs when the soft tissue is removed from the vertebrae, generally with a device that scrapes along the hard vertebrae surface and simultaneously strips the soft tissue from the vertebrae. Generally the soft tissue is first removed from the vertebrae with a first handheld non-powered instrument, and then the separated tissue is treated to reduce blood loss with a second instrument, typically an electrosurgical monopolar (Bovie) pencil. What is needed is a single surgical instrument which reduces the need to switch between different instruments, and offers the surgeon the ability to treat tissue against blood loss simultaneously with the separation of soft tissue from bone, resulting in reduced surgical time.

SUMMARY OF THE INVENTION

According to one aspect of the present invention, a bipolar electrosurgical scraper device is provided comprising a handle, a blade having a thickness and a beveled distal end with the beveled distal end terminating distally in a scraping edge. The beveled distal end includes a first electrode and a second electrode with the first electrode and the second electrode provided along a width of the blade and spaced apart with respect to the thickness of the blade. The device also comprises a fluid passage and at least one fluid outlet in fluid communication with the fluid passage.

According to another aspect of the present invention, a bipolar electrosurgical scraper device is provided comprising a handle, a blade having a thickness and a beveled distal end with the beveled distal end terminating distally in a scraping edge. The beveled distal end includes a first electrode and a second electrode with the first electrode and the second electrode comprising two strips along a width of the blade and spaced apart with respect to the thickness of the blade. The device also comprises a fluid passage and at least one fluid outlet in fluid communication with the fluid passage.

According to one aspect of the invention, the scraping edge of the device may be straight or curved, and in particular semi-circular.

According to another aspect of the invention, the first electrode and the second electrode may be provided along a center portion of the width of the blade, along a substantial portion of the width of the blade or along the complete width of the blade.

According to another aspect of the invention, the beveled distal end is at a bevel angle with respect to a longitudinal axis of the device, and the bevel angle may be in the range between and including about 20 degrees to 70 degrees, in the range between and including about 30 degrees to 60 degrees or 30 degrees.

According to another aspect of the invention, the blade further comprises a front side and a back side, the beveled distal end is at a bevel angle with respect to a longitudinal axis of the device and the bevel angle is uniform from the front side to the back side of the blade.

According to another aspect of the invention, the beveled distal end is at a bevel angle with respect to a longitudinal axis of the device; and the bevel angle is uniform along the thickness of the blade.

According to another aspect of the invention, the beveled distal end comprises an electrical insulator with the electrical insulator located between the first electrode and the second electrode.

According to another aspect of the invention, the blade comprises a layered structure with respect to the thickness of the blade, the layered structure comprising an intermediate insulating member disposed between a first metal member and a second metal member, with the first metal member serving as the first electrode, the second metal member serving as the second electrode and one of the first metal member and second metal member providing the scraping edge.

BRIEF DESCRIPTION OF THE DRAWINGS

To better understand and appreciate the invention, reference is made to the following detailed description in connection with the accompanying drawings, hand and/or computer generated:

FIG. 2 is front view of the device of FIG. 1;

FIG. 3 is a rear view of the device of FIG. 1;

FIG. 4 is a cross-sectional view taken along line 4-4 of FIG. 2;

FIG. 5 is a close-up of the tip portion within the circle of FIG. 4;

FIG. 9 is a side view of the tip portion;

FIG. 10 is a cross-sectional view taken along line 10-10 of FIG. 9;

DETAILED DESCRIPTION

Figure 1:
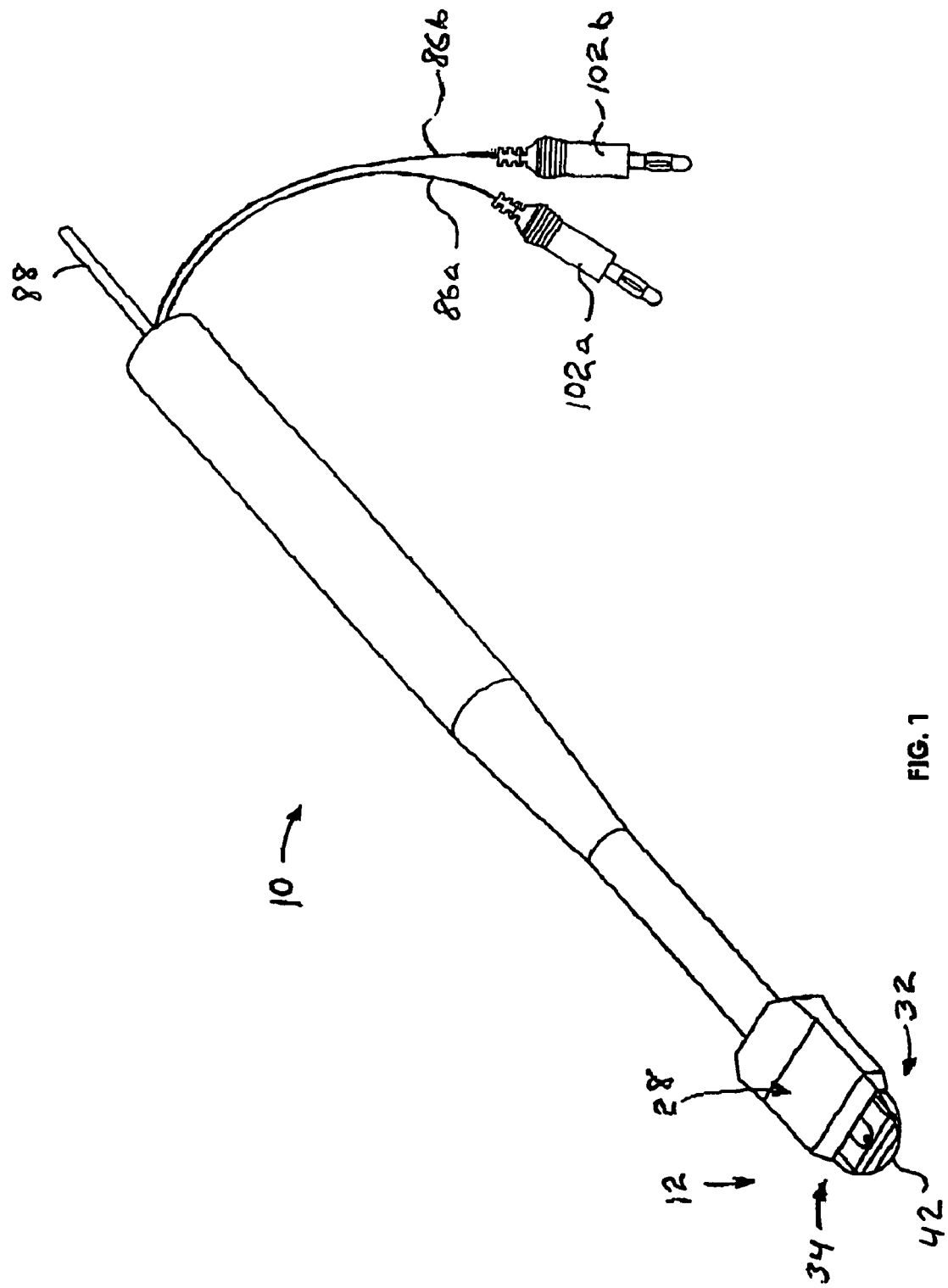
FIG. 1 is a perspective view of an electrosurgical device according to the present invention.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive.

Reference will now be made to the preferred embodiments of the invention, examples of which are illustrated in the accompanying drawings. While the preferred embodiments of the invention describe medical devices and methods of use, it should be understood that their combination is for purposes of illustration only. In other words, it should be understood that the use of the medical devices of the present invention is not limited to any methods disclosed herein. Conversely, it should be equally understood that the methods of the present invention can potentially be used with a wide variety of medical devices.

An exemplary electrosurgical device of the present invention is shown at reference character 10 throughout the figures. As shown in FIG. 1, electrosurgical device 10 more specifically comprises a fluid-assisted bipolar electrosurgical device. With a bipolar device, in the presence of alternating current, an electrical circuit is created with the electrodes of the device, which alternate in polarity between positive and negative charges with the current flow from the positive to the negative charge.

As shown in FIGS. 2 and 3, electrosurgical device 10 has a working tip portion 12 and a handle 16 for grasping device 10 and manipulating tip portion 12. As shown in FIG. 4, handle 16 preferably includes a cylindrical hand grip member 18 which has an electrically insulative material, such as a synthetic polymer, overlying a support (reinforcement) arm 14. Support arm 14 preferably comprises a hollow metal cylinder provided, for example, by stainless steel tubing having a substantially uniform diameter along its length. Support arm 14 and hand grip member 18 are interconnected by having at least a portion of support arm 14 inserted into a bore 22 in hand grip member 18. In the embodiment shown, hand grip member 18 completely covers arm 14, but in other embodiments only a portion of arm 14 may be covered, such as only a proximal portion. Also, in other embodiments, support arm 14 may be deleted.

As best seen in FIGS. 2 and 4, tip portion 12 is blade shaped and comprises a front-side 28 and a rear-side 30, and flanking (lateral) left-side 32 and right-side 34. As best seen in FIG. 5, front-side 28 has a front-side planar surface 36 which is parallel with rear-side planar surface 38. At the distal end of device 10, the transition between front-side surface 36 and rear-side surface 38 includes a bevel surface 40, which forms a bevel angle A with rear-side surface 38.

Preferably, bevel angle A should be in the range between and including about 10 degrees to 80 degrees, and more preferably in the range between and including about 20 degrees to 70 degrees. Even more preferably, bevel angle A should be in the range between and including about 30 degrees to 60 degrees. As shown in this embodiment, bevel angle A is 30 degrees.

Figure 6:
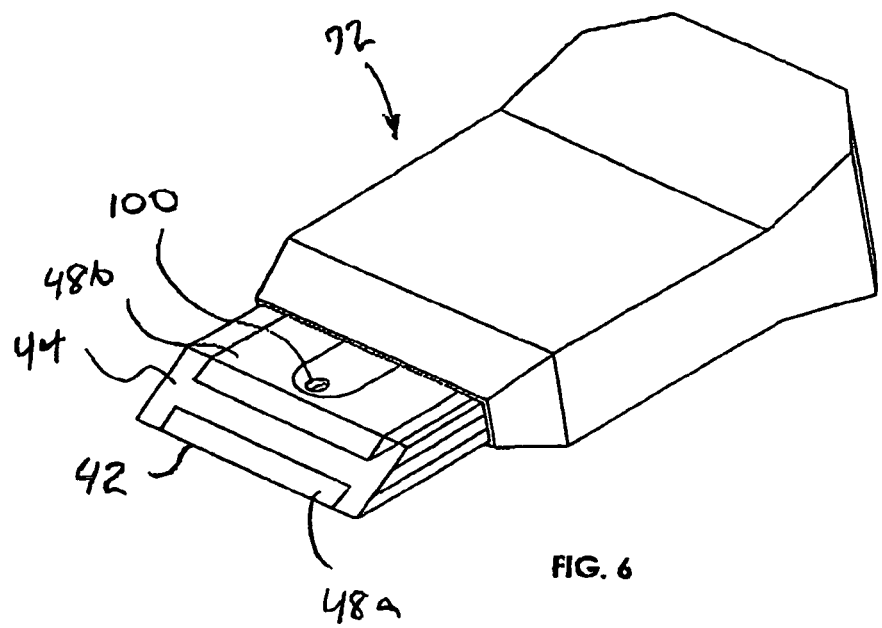
FIG. 6 is an alternative embodiment of the tip portion.

Also best shown in FIG. 5, rear-side surface 38 and bevel surface 40 extend distally to a distal leading sharp scraping/cutting edge 42. Referring back to FIG. 3, leading edge 42 is preferably curved (e.g., semi-circular) outwardly along the width W of tip portion 12 with respect to the length L of device 10. In other embodiments, as shown in FIG. 6, leading edge 42 may be straight as opposed to curved.

Tip portion 12 has a width W preferably in the range of 0.125 inch (3 mm) to 1 inch (25 mm), with the preferred width W depending notably on the size of the treatment site and the ability to successfully navigate within the treatment site. Device 10 may be provided as part of a kit including devices 10 having varying widths, either based on a metric units (e.g. 3 mm, 4 mm, 5 mm, . . . 25 mm) or standard (English) units (e.g. 1/8 inch, 1/4 inch, 1/2 inch, 5/8 inch, 3/4 inch, 1 inch).

Figure 7:
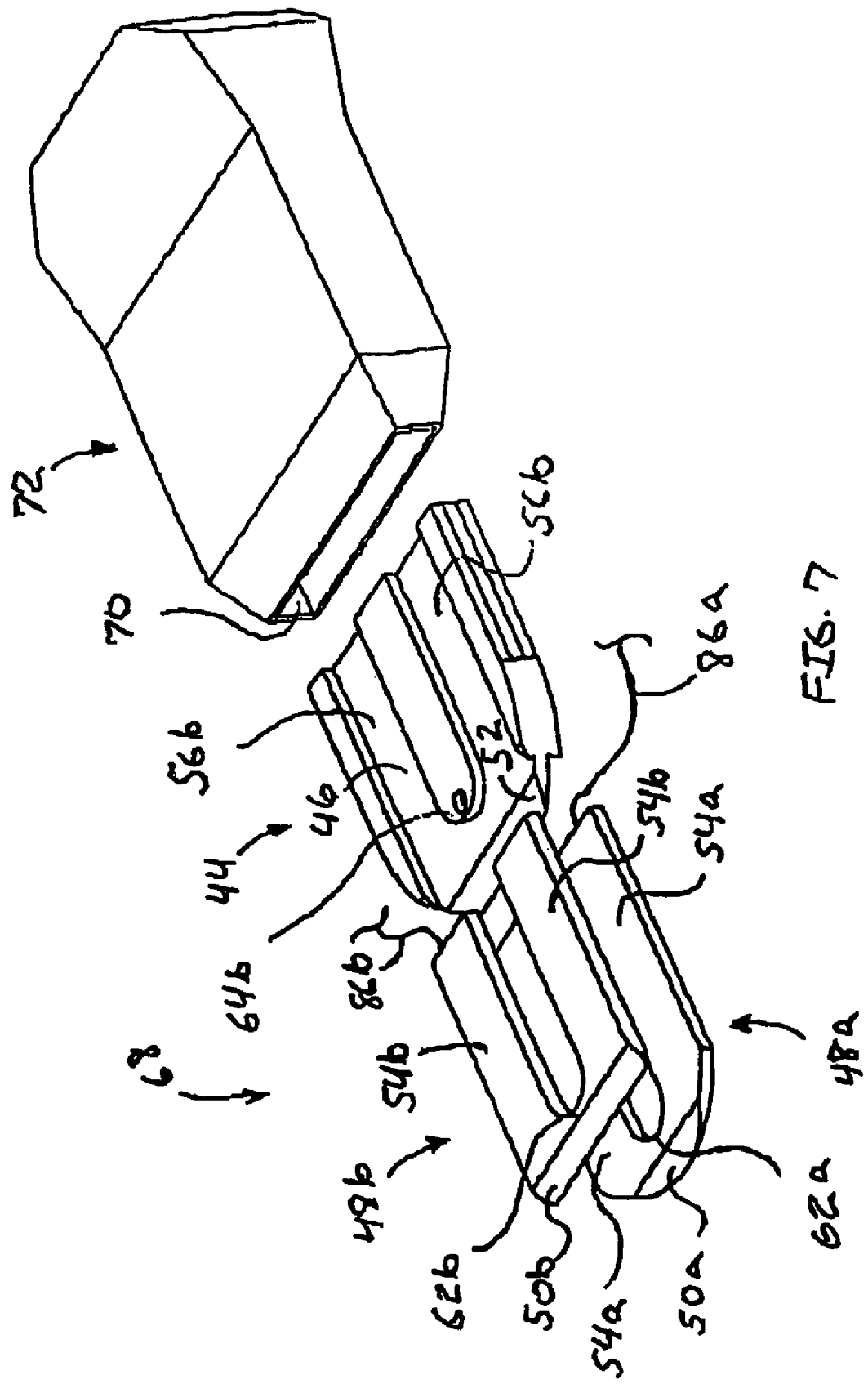
FIG. 7 is an exploded close-up perspective view of the tip portion.

As best shown in FIG. 7, tip portion 12 comprises an electrode support member 44, which comprises an electrically insulative material, preferably a polymer and more preferably a fluorinated polymer such as polytetrafluoroethylene (PTFE). In addition to functioning as a electrical insulator, polytetrafluoroethylene is preferred because it is hydrophobic and thus inhibits fluids present during surgery from settling thereon, provides good arc resistance, and provides a low coefficient of friction for reduced tissue sticking.

As shown in FIG. 7, support member 44 provides an intermediate support pedestal 46 positioned in a sandwich type layered structure between two metal blade shaped electrodes 48a, 48b which are electrically coupled to an energy source such as a generator. Electrodes 48a, 48b provide a portion of front-side surface 36 and rear-side surface 38, respectively. Also as shown, the distal end surfaces 50a, 50b of electrodes 48a, 48b and the distal end surface 52 of support member 44 all provide a portion of bevel surface 40.

Continuing with FIG. 7, the distal end surfaces 50a, 50b of electrodes 48a, 48b and the distal end surface 52 of support member 44 are preferably all provided such that bevel surface 40 is substantially planar along its length from rear-side surface 38 to front-side surface 36. As best shown in FIG. 5, electrodes 48a, 48b and support member 44 all preferably individually have a bevel angles which are each equal to bevel angle A, thus maintaining a uniform bevel angle through the thickness T of tip portion 12 from rear-side surface 38 to front-side surface 36.

Figure 8:
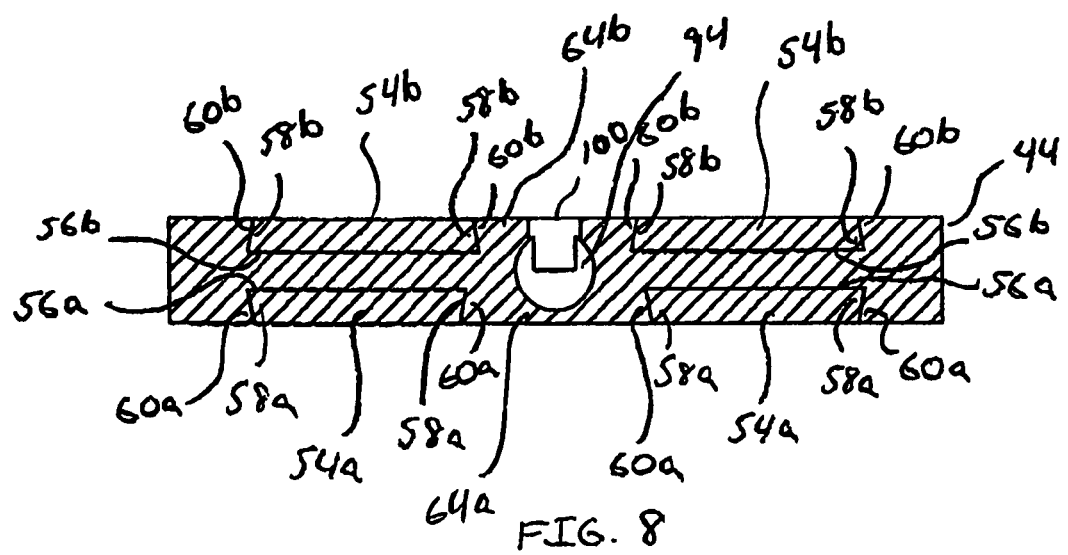
FIG. 8 is a cross-sectional view taken along line 8-8 of FIG. 2.

As shown in FIG. 8, preferably electrodes 48a, 48b are assembled to support member 44 by means of an interlocking joint which provides mechanical engagement between the pieces and restricts their separation, and also assists positioning the pieces relative to one another. As shown, preferably each electrode 48a, 48b is formed with a pair of elongated, parallel, longitudinally oriented flared tenons 54a, 54b which slide in proximally and cooperate with a pair of elongated, parallel undercut mortises 56a, 56b formed in support member 44 which results in a dovetail joint when assembled. With this configuration, a mechanical engagement which restricts the layers from planar separation is created between the flared portion 58a, 58b of tenons 54a, 54b and undercut portions 60a, 60b of mortises 56a, 56b.

As best shown in FIG. 7, the flared tenons 54a, 54b of each electrode 48a, 48b are configured to slide proximally into the undercut mortises 56a, 56b formed in support member 44 until a center span portion 62a, 62b of each electrode 48a, 48b makes contact with a shoulder 64a, 64b. After electrodes 48a, 48b have been assembled to support member 44, a proximal portion 66 of the working tip assembly 68 is inserted into rectangular receptacle 70 of tip assembly housing 72.

As shown in FIGS. 9 and 10, proximal portion 66 of tip assembly 68 extends into receptacle 70 provided by a portion of cavity 73 such that the proximal end 74 of tip assembly 68 is positioned against shoulder 76 of housing 72. In order to inhibit the separation of tip assembly 68 from housing 72, preferably the proximal portion 66 of tip assembly 68 is press (interference) fit into receptacle 70.

As best shown in FIG. 5, support arm 14 is preferably assembled to tip assembly housing 72 by inserting a distal portion 78 of support arm 14 into circular receptacle 80. As shown, distal portion 78 of arm 14 extends into receptacle 80 such that the distal end 82 of arm 14 is positioned against shoulder 84 of housing 72. In order to inhibit the separation of arm 14 from housing 72, preferably the distal portion 78 of arm 14 is press (interference) fit into receptacle 80.

Figure 11:
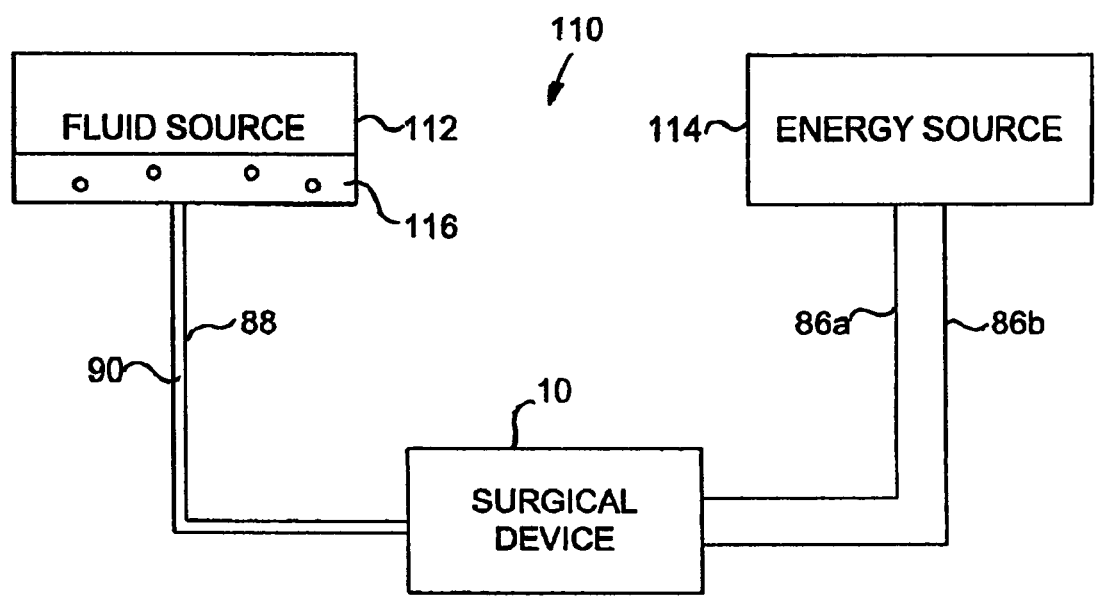
FIG. 11 is a block diagram of an electrosurgical system used with device of FIG. 1.

As shown in FIG. 11, electrosurgical device 10 is preferably used as part of a system 110 comprising a fluid source 112 and an electrical energy source 114. As shown, electrosurgical device 10 is preferably coupled to energy source 114 via insulated wire conductors 86a, 86b. With respect to the fluid coupling, fluid 116 from the fluid source 112 is preferably communicated from fluid source 112 to electrosurgical device 10 through a flexible, polyvinylchloride (PVC) fluid line 88 having a fluid passage (lumen) 90.

Energy source 114 preferably comprises a generator, and more preferably a radio frequency alternating current generator which may provide radio frequency power therefrom at selected increments. Fluid source 112 preferably comprises an intravenous bag containing electrically conductive fluid, which more preferably comprises saline. More preferably, the saline comprises sterile, and even more preferably, normal saline. Although the description herein will specifically describe the use of saline as the fluid, other electrically conductive fluids, as well as non-conductive fluids, can be used in accordance with the invention.

For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

As best shown in FIG. 5, a distal portion 89 of fluid line 88 is preferably interference fit over the outside diameter of a proximal portion 91 of a hollow coupling tube 92 to provide a press fit seal there between. A distal portion 93 of coupling tube 92 is inserted and interference fit in a distally extending bore 94 within support member 44. Fluid 116 from fluid passage 90 of fluid line 88 flows therefrom into fluid passage 96 of coupling tube 92 and thereafter into fluid passage 98 provided by bore 94 where is finally expelled from fluid outlet opening 100 in top side 28.

As shown in FIG. 11, radio frequency energy for electrodes 48a, 48b is provided from electrical energy source 114 through insulated wire conductors 86a, 86b. Preferably, wire conductors 86a, 86b reach electrodes 48a, 48b by traveling through bore 20 of arm 14 and thereafter through cavity 73 of housing 72. As shown in FIG. 7, wire conductors 86a, 86b are electrically coupled (e.g. welded) to electrodes 48a, 48b, and connectable to energy source 114 via two connectors 102a, 102b (such as banana (male) plug connectors) as shown in FIG. 1.

Figure 12:
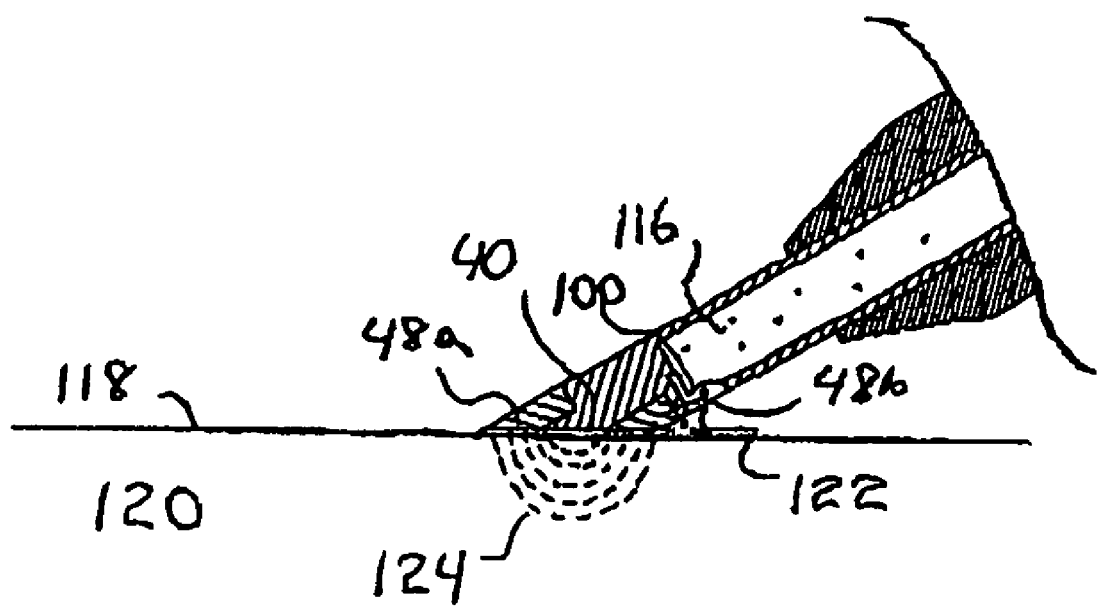
FIG. 12 is a close-up cross-sectional view of the tip portion in the presence of tissue.

As best shown in FIG. 12, when device 10 is in use as a sealer to inhibit bleeding, electrodes 48a, 48b are preferably positioned adjacent tissue surface 118 of tissue 120. As shown, the electrodes 48a, 48b are fluidly coupled to the surface 118 of tissue 120 by a fluid coupling 122 which provides a film of fluid 116 between surface 118 of tissue 120 and bevel surface 40 of device 10. When the user of electrosurgical device 10 places electrodes 48a, 48b at a tissue treatment site and moves electrodes 48a, 48b across surface 118 of tissue 120, fluid 116 is being expelled from outlet opening 100 and at the same time, radio frequency electrical energy (current), as shown by electrical field lines 124, is provided to tissue 120 at tissue surface 118 and below tissue surface 118 into tissue 120 through the fluid coupling 122.

In addition to fluid 116 providing an electrical coupling between the electrosurgical device 10 and tissue 120, fluid 116 lubricates surface 118 of tissue 120 and facilitates the movement of electrodes 48a, 48b across surface 118 of tissue 120. During movement of electrodes 48a, 48b, electrodes 48a, 48b typically slide across the surface 118 of tissue 120. Typically the user of electrosurgical device 10 slides electrodes 48a, 48b across surface 118 of tissue 120 by moving device 10 with repetitive strokes, while using fluid 116 as, among other things, a lubricating coating. Preferably the thickness of the fluid 116 between the electrodes 48a, 48b and surface 118 of tissue 120 is in the range between and including about 0.05 mm to 1.5 mm, and more preferably in the range between and including about 0.1 mm to 0.3 mm. In certain embodiments, the electrodes 48a, 48b may contact surface 118 of tissue 120 without any fluid 116 in between.

With use of electrosurgical device 10, the heating of the tissue 120 is generated due to the electrical resistance of the tissue 120. In other words, increasing the temperature of the tissue 120 as a result of electric current flow through the tissue 120, with the electrical energy being absorbed from the voltage and transformed into thermal energy (i.e. heat) via accelerated movement of ions as a function of the tissue's electrical resistance.

Device 10 is particularly useful to a surgeon as a tissue coagulator and sealer which seals tissue from the flow of bodily fluids (e.g. blood) by shrinking the tissue. As known in the art, when exposed to heat, the collagen of the blood vessels will shrink, thus decreasing the diameter and associated lumen of the vessel. With use of device 10, certain vessels, depending on size and proximity to surface of tissue will become completely occluded, while other vessels, such as deep or particularly large vessels, may become only partially occluded initially, and need additional treatment with device 10 to become completely occluded as the device 10 is used to coag and cut deeper into the tissue. During use, device 10 can be moved over a raw (untreated), oozing surface of tissue to seal the tissue against bleeding, or focused on individual large vessels, such as to seal a bleeding vessel which has been cut, or to occlude a vessel prior to being cut.

With its wedge/chisel shape, device 10 is also particularly useful as a tissue cutter and separator to separate tissue adjacent bone (e.g. connective tissue such as muscle, tendons, ligaments and periosteum) with a wedge technique, and seal the tissue which has been separated from the bone. In a spine procedure, for example, such as a device 10 may be used to separate soft tissue from the vertebrae of the spine. More specifically, device 10 may be used to separate soft tissue from the various portions of the vertebrae, such as the vertebral arch, vertebral body, various processes (e.g. spinous process, transverse process, annular process, inferior articular process, superior articular process) and various facets (superior articular facet, inferior articular facet).

Figure 13:
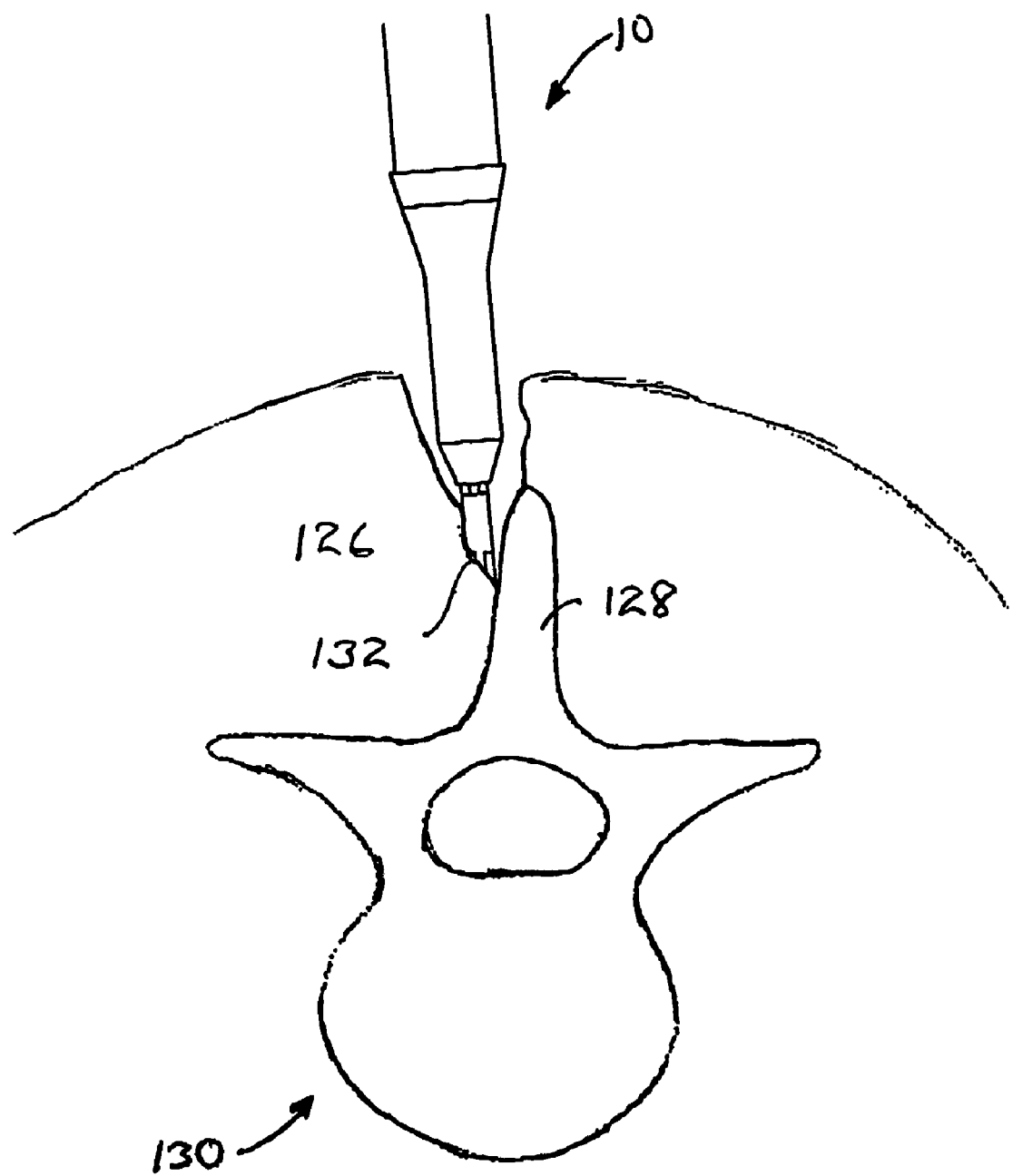
FIG. 13 is a side view of the tip portion being used to remove tissue from a human vertebrae.

As shown in FIG. 13, as part of an osteotomy of the spine to correct a spinal deformity resulting from, for example, scoliosis, device 10 separates erector spinae muscle 126 from the spinous process 128 of the vertebrae 130 by cutting the periosteum 132 and wedging device 10 between the erector spinae muscle 126 and the spinous process 128 while simultaneously using device 10 as a retractor against erector spinae muscle 126 and sealing the severed periosteum 132 against blood loss.

In other embodiments, electrosurgical device 10 may comprise a single electrode 48 and be a monopolar device. With use of a monopolar device, the first electrode, often referred to as the active electrode, comprises electrode 48 of the electrosurgical device 10 while a second electrode, often referred to as the indifferent or return electrode, comprises a ground pad dispersive electrode located on the patient and coupled to energy source 114, typically on the back or other suitable anatomical location. An electrical circuit is formed between electrode 48 and ground pad dispersive electrode with electrical current flowing from electrode 48 through the patient to ground pad dispersive electrode in a manner known in the art.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents.

Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes, to the extent they are consistent.

What is claimed is:

1. A bipolar electrosurgical scraper device comprising:
a handle;
a blade distal to the handle, the blade having a front side, a rear side, a thickness and a beveled distal end, the beveled distal end terminating distally in a scraping edge at the rear side of the blade;
the beveled distal end including a first electrode and a second electrode, the first electrode and the second electrode provided along a width of the blade and spaced apart with respect to the thickness of the blade, wherein the beveled distal end is at a bevel angle with respect to a longitudinal axis of the device, and wherein the bevel angle is uniform along the thickness of the blade;
a fluid passage extending distally with the handle; and
at least one fluid outlet in fluid communication with the fluid passage.

2. The device of claim 1 wherein:
the scraping edge is straight.

3. The device of claim 1 wherein:
the first electrode and the second electrode are provided along a center portion of the width of the blade.

4. The device of claim 1 wherein:
the first electrode and the second electrode are provided along a substantial portion of the width of the blade.

5. The device of claim 1 wherein:
the bevel angle in the range between and including about 20 degrees to 70 degrees.

6. The device of claim 1 wherein:
the bevel angle in the range between and including about 30 degrees to 60 degrees.

7. The device of claim 1 wherein:
the bevel angle at 30 degrees.

8. The device of claim 1 wherein:
the bevel angle is uniform from the front side to the rear side of the blade.

9. The device of claim 1 wherein:
the beveled distal end further comprises an electrical insulator, the electrical insulator located between the first electrode and the second electrode.

10. The device of claim 9 wherein:
the electrical insulator comprises a polymer.

11. The device of claim 1 wherein:
the blade further comprises a layered structure with respect to the thickness of the blade, the layered structure comprising an intermediate insulating member disposed between the first electrode and the second electrode.

12. The device of claim 11 wherein:
one of the first electrode and second electrode provides the scraping edge.

13. The device of claim 11 wherein:
the layered blade structure is restricted from separation by a dovetail joint.

14. A bipolar electrosurgical scraper device comprising:
a handle;
a blade distal to the handle, the blade having a front side, a rear side, a thickness and a beveled distal end, the beveled distal end terminating distally in a scraping edge at the rear side of the blade;
the beveled distal end including a first electrode and a second electrode, the first electrode and the second electrode comprising two strips along a width of the blade and spaced apart with respect to the thickness of the blade, wherein the beveled distal end is at a bevel angle with respect to a longitudinal axis of the device, and wherein the bevel angle is uniform along the thickness of the blade;
a fluid passage extending distally with the handle; and
at least one fluid outlet in fluid communication with the fluid passage.

15. The device of claim 14 wherein:
the scraping edge is straight.

16. The device of claim 14 wherein:
the first electrode and the second electrode are provided along a center portion of the width of the blade.

17. The device of claim 14 wherein:
the bevel angle in the range between and including about 20 degrees to 70 degrees.

18. The device of claim 14 wherein:
the beveled distal end further comprises an electrical insulator, the electrical insulator located between the first electrode and the second electrode.

19. The device of claim 14 wherein:
the blade further comprises a layered structure with respect to the thickness of the blade, the layered structure comprising an intermediate insulating member disposed between the first electrode and the second electrode.

20. The device of claim 14 wherein:
one of the first electrode and second electrode provides the scraping edge.

* * * * *

UNITED STATES PATENT AND TRADEMARK OFFICE
CERTIFICATE OF CORRECTION

| | | Page 1 of 1 |
|---|---|---|
| PATENT NO. | : 7,727,232 B1 | |
| APPLICATION NO. | : 11/051090 | |
| DATED | : June 1, 2010 | |
| INVENTOR(S) | : Christopher W. Maurer et al. | |

It is certified that error appears in the above-identified patent and that said Letters Patent is hereby corrected as shown below:

On the title page, below item (22), column 1, insert -- Related U.S. Application Data
(60) Provisional application No. 60/541,997, filed on Feb. 4, 2004. --.

Signed and Sealed this
Twenty-third Day of August, 2011

David J. Kappos
*Director of the United States Patent and Trademark Office*